United States Patent
Takahashi et al.

[11] Patent Number: 6,121,470
[45] Date of Patent: Sep. 19, 2000

[54] GLYCINE DERIVATIVES, INTERMEDIATES THEREFOR AND CLEANSER COMPOSITIONS COMPRISING THEM

[75] Inventors: Masakatsu Takahashi; Hiromoto Mizushima, both of Wakayama; Hiroe Tanahashi, Tokyo; Toshio Nozaki, Sakaemachi, all of Japan

[73] Assignee: Kao Corporation, Tokyo, Japan

[21] Appl. No.: 08/704,775

[22] PCT Filed: Mar. 28, 1995

[86] PCT No.: PCT/JP95/00581

§ 371 Date: Sep. 23, 1996

§ 102(e) Date: Sep. 23, 1996

[87] PCT Pub. No.: WO95/26329

PCT Pub. Date: Oct. 5, 1995

[30] Foreign Application Priority Data

Mar. 29, 1994 [JP] Japan ................................. 6-058853

[51] Int. Cl.[7] ........................ C07C 233/00; C07C 231/00
[52] U.S. Cl. ................. 554/54; 554/63; 554/68; 554/69; 562/484; 562/553; 562/571; 510/126; 510/130; 510/218; 510/221; 510/235
[58] Field of Search ................... 554/54, 63, 68, 554/69; 562/553, 571, 484; 510/126, 130, 218, 221, 235

[56] References Cited

U.S. PATENT DOCUMENTS 4,650,613  3/1987  Pulwer et al. .

OTHER PUBLICATIONS

Chem. Abstr. 119: 141674, 1995.

*Primary Examiner*—Deborah D. Carr
*Attorney, Agent, or Firm*—Oblon, Spivak, McClelland, Maier & Neustadt, P.C.

[57] ABSTRACT

Glycine derivatives represented by the following formula (1) and cleanser compositions containing the same:

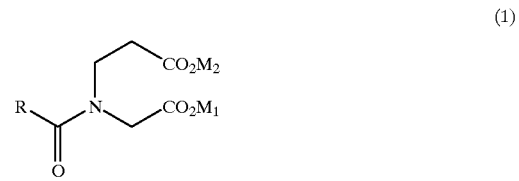

(1)

wherein R is a linear or branched alkyl group having 11 to 13 carbon atoms, a linear or branched alkenyl group having 11 to 13 carbon atoms, or a linear or branched hydroxyalkyl group having 11 to 13 carbon atoms, and $M_1$ and $M_2$ are the same or different from each other and each independently is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid, are excellent in foaming, detergency, comfort in use and safety, are antipollutive and can be used for various purposes, for example, a cleanser composition for the hair and body or tableware.

22 Claims, 2 Drawing Sheets

GLYCINE DERIVATIVES, INTERMEDIATES THEREFOR AND CLEANSER COMPOSITIONS COMPRISING THEM

This application is a 371 of PCT/JP95/00581 filed Mar. 28, 1995.

BACKGROUND OF THE INVENTION

1. Field of the Invention

The present invention relates to novel glycine derivatives of low skin irritancy and high foaming power, processes for producing the same, and cleanser compositions containing such glycine derivatives.

Further, the present invention relates to other glycine derivatives which are useful as intermediates for synthesizing the above-mentioned glycine derivatives and are themselves useful as cleansers, processes for producing the same, and cleanser compositions containing such glycine derivatives.

Furthermore, the present invention relates to a method of washing skin or hair using such a cleanser composition, i.e., an use of the cleanser composition.

The cleanser compositions of the present invention exhibit excellent foaming, are free from sliminess and stickiness and exhibit excellent foam breaking during rinsing, have reduced irritancy toward the skin and are excellent in storage stability.

2. Discussion of the Background

In recent years, it has become necessary to minimize the effects that surfactants to be used as cleansers on the environment. In other words, it has become necessary that the surfactants be excellent in biodegradability and safety, and exhibit reduced irritancy toward the skin and eyes. Various surfactants such as acylated amino acids, imidazoline surfactants, alkyl phosphate salts, betaine surfactants and saccharide surfactants have been developed and employed as surfactants meeting these requirements.

Although these surfactants are excellent in environmental protection and safety, their foaming powers and detergencies are generally unsatisfactory. Therefore, the surfactants that are generally used for, e.g., a shampoo, a body cleanser, a tableware detergent are still anionic surfactants such as higher fatty acid salts (soaps), alkyl sulfates (AS), polyoxyethylene alkyl ether sulfates (ES) and alkyl sulfonates, and the aforementioned surfactants are only used as auxiliaries.

When, for example, soap is used for skin cleansing, soap scum (Ca salt of higher fatty acid) is formed and adheres to the skin during rinsing, so that the smoothness of the skin surface is remarkably lowered to result in squeakiness and stiffness. When an alkyl sulfate or an alkyl sulfonate is used for skin cleansing, it is poor in foam breaking and causes a problem with respect to comport in use such as sliminess and stickiness, though it does not result in squeakiness and stiffness.

Therefore, various auxiliaries such as oils, e.g., a higher alcohol, and auxiliary cleansers are contained in cleanser compositions such as shampoos, body cleansers and tableware detergents. However, the empolyment of such auxiliaries leads to a degradation of the detergency, foaming power, comfort in use and the like, so that the types and the amounts of the auxiliaries which can be used are subject to various restraints. Thus, it has been difficult to obtain cleanser compositions having satisfactory performances.

Under these circumstances, cleanser compositions each containing an anionic surfactant of an acylimino dibasic acid type have been proposed [see Japanese Patent Publication-A Nos. 54-30207 (published on Mar. 6, 1979), 5-117139 (published on May 14, 1993) and-6-80987 (published on Mar. 22, 1994)]. Although these cleanser compositions are improved in detergency, foaming power and comfort in use, as compared with those in the prior art, they have a drawback in that the storage stability at, especially, low temperatures is poor, because the anionic surfactants of the acylimino dibasic acid type are derivative of an iminodiacetic acid.

Consequently, the development of surfactants which are excellent in environmental protection and safety, exhibit high foaming power and detergency, are excellent the comfort in use and can be used for various purposes is strongly demanded in the art. There also remains a need for such surfactants which exhibit excellent storage stability when used as one component of a cleanser composition.

SUMMARY OF THE INVENTION

Accordingly, it is one object of the present invention to provide novel surfactants.

It is another object of the present invention to provide surfactants with excellent environmental protection, safety, foaming power, detergency and comfort in use and with applicability for various purposes which are useful as cleansers for the hair, body and tableware.

It is another object of the present invention to provide novel processes for producing such surfactants.

It is another object of the present invention to provide novel intermediates for preparing such surfactants.

It is another object of the present invention to provide novel processes for producing such intermediates.

It is another object of the present invention to provide novel compositions which contain such surfactants.

It is another object of the present invention to provide novel compositions which contain such surfactants, exhibit excellent foaming and foam stability, are free from sliminess and stickiness and exhibit excellent foam breaking during rinsing, have reduced irritancy and are excellent in storage stability at low temperatures.

It is another object of the present invention to provide a novel method of washing skin or hair with such a composition.

It is another object of the present invention to provide a novel use of such a composition for the washing of skin or hair.

These and other objects, which will become apparent during the following detailed description, have been achieved by the inventors' discovery that amide surfactants each having two hydrophilic groups derived from glycine are excellent in environmental protection and safety, have high foaming power and detergency, are excellent comfort in use, and can be used for various purposes.

Further, these and other objects have been achieved by the inventors' discovery that the cleanser compositions comprising an amide surfactant having two hydrophilic groups derived from glycine and a specific sugar surfactant, a specific ether-type acetic acid surfactant or a specific fatty acid amide derivative are excellent in foaming and foam stability, are free from sliminess and stickiness and exhibit excellent foam breaking during rinsing, have reduced irritancy, and are excellent in storage stability at low temperatures.

Thus, the present invention provides glycine derivatives represented by the following formulas (1) to (4):

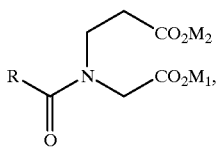
(1)

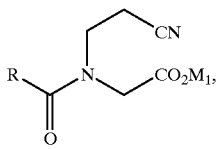
(2)

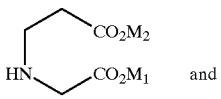 and
(3)

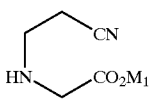
(4)

wherein R is a linear or branched alkyl group having 11 to 13 carbon atoms, a linear or branched alkenyl group having 11 to 13 carbon atoms, or a linear or branched hydroxyalkyl group having 11 to 13 carbon atoms, and $M_1$ and $M_2$ are the same or different from each other and each independently is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid.

Thus, the present invention provides:

i) a process for producing the glycine derivative represented by the above formula (1) which comprises hydrolyzing the cyano group of the glycine derivative represented by the above formula (2), optionally followed by salt exchange;

ii) a process for producing the glycine derivative represented by the above formula (1) which comprises reacting the glycine derivative represented by the above formula (3) with an acid chloride represented by the formula: RCOCl (wherein R is as defined above) (6), optionally followed by salt exchange;

iii) a process for producing the glycine derivative represented by the above formula (1) which comprises a step of reacting glycine or a salt thereof represented by the formula:

(wherein $M_1$ is as defined above) (5) with acrylonitrile;

iv) a process for producing the glycine derivative represented by the above formula (1) which comprises a step of reacting glycine or a salt thereof represented by the formula:

(wherein $M_1$ is as defined above) (5) with alcrylonitrile to give the glycine derivative represented by the above formula (4), and a step of reacting the glycine derivative represented by the above formula (4) with an acid chloride represented by the formula: RCOCl (wherein R is as defined above) (6), optionally followed by salt exchange;

v) a process for producing the glycine derivative represented by the above formula (1) which comprises a step of reacting glycine or a salt thereof represented by the formula:

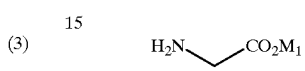

(wherein $M_1$ is as defined above) (5) with acrylonitrile to give the glycine derivative represented by the above formula (4), and a step of hydrolyzing the cyano group of the glycine derivative represented by the above formula (4), optionally followed by salt exchange;

vi) a process for producing the glycine derivative represented by the above formula (1) which comprises a step of reacting glycine or a salt thereof represented by the formula:

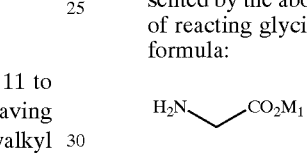

(wherein $M_1$ is as defined above) (5) with acrylonitrile to give the glycine derivative represented by the above formula (4), a step of reacting the glycine derivative represented by the above formula (4) with an acid chloride represented by the formula: RCOCl (wherein R is as defined above) (6), optionally followed by salt exchange to give the glycine derivative represented by the above formula (2), and a step of hydrolyzing the cyano group of the glycine derivative represented by the above formula (2), optionally followed by salt exchange;

vii) a process for producing the glycine derivative represented by the above formula (1) which comprises a step of reacting glycine or a salt thereof represented by the formula:

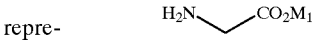

(wherein $M_1$ is as defined above) (5) with acrylonitrile to give the glycine derivative represented by the above formula (4), a step of hydrolyzing the cyano group of the glycine derivative represented by the above formula (4), optionally followed by salt exchange to give the glycine derivative represented by the above formula (3), and a step of reacting the glycine derivative represented by the above formula (3) with an acid chloride represented by the formula: RCOCl (wherein R is as defined above) (6), optionally followed by salt exchange;

viii) a process for producing the glycine derivative represented by the above formula (1) which comprises using the glycine derivative represented by the above formula (2); and ix) a process for producing the glycine derivative represented by the above formula (1) which comprises using the glycine derivative represented by the above formula (4).

Further, the present invention provides:
i) a process for producing the glycine derivative represented by the above formula (2) which comprises reacting the glycine derivative represented by the above formula (4) with an acid chloride represented by the formula: RCOCl (wherein R is as defined above) (6), optionally followed by salt exchange;
ii) a process for producing the glycine derivative represented by the above formula (2) which comprises a step of reacting glycine or a salt thereof represented by the formula:

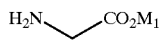

(wherein $M_1$ is as defined above) (5) with acrylonitrile;
iii) a process for producing the glycine derivative represented by the above formula (2) which comprises a step of reacting glycine or a salt thereof represented by the formula:

(wherein $M_1$ is as defined above) (5) with acrylonitrile to give the glycine derivative represented by the above formula (4), and a step of reacting the glycine derivative represented by the above formula (4) with an acid chloride represented by the formula: RCOCl (wherein R is as defined above) (6), optionally followed by salt exchange; and
iv) a process for producing the glycine derivative represented by the above formula (2) which comprises using the glycine derivative represented by the above formula (4).

Furthermore, the present invention provides:
i) a process for producing the glycine derivative represented by the above formula (3) which comprises hydrolyzing the cyano group of the glycine derivative represented by the above formula (4), optionally followed by salt exchange;
ii) a process for producing the glycine derivative represented by the above formula (3) which comprises a step of reacting glycine or a salt thereof represented by the formula:

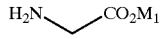

(wherein $M_1$ is as defined above) (5) with acrylonitrile;
iii) a process for producing the glycine derivative represented by the above formula (3) which comprises a step of reacting glycine or a salt thereof represented by the formula:

(wherein $M_1$ is as defined above) (5) with acrylonitrile to give the glycine derivative represented by the above formula (4), and a step of hydrolyzing the cyano group of the glycine derivative represented by the above formula (4), optionally followed by salt exchange; and
iv) a process for producing the glycine derivative represented by the above formula (3) which comprises using the glycine derivative represented by the above formula (4).

In addition, the present invention provides a process for producing a glycine derivative represented by the above formula (4) which comprises reacting glycine or a salt thereof represented by the formula:

(wherein $M_1$ is as defined above) (5) with acrylonitrile.
The present invention also provides:
i) a cleanser composition comprising the glycine derivative represented by the above formula (1);
ii) a cleanser composition comprising the glycine derivative represented by the above formula (1) and a sugar surfactant represented by the formula: $R^1$—$(OR^2)_m$—$G_n$ (wherein $R^1$ is a linear or branched alkyl group having 8 to 18 carbon atoms, a linear or branched alkenyl group having 8 to 18 carbon atoms, or a substituted phenyl group having a linear or branched alkyl group of 8 to 18 carbon atoms, $R^2$ is an alkylene group having 2 to 4 carbon atoms, G is a residue derived from a reducing sugar having 5 to 6 carbon atoms, m is a number of 0 to 10 and n is a number of 1 to 10) (7);
iii) a cleanser composition comprising the glycine derivative represented by the above formula (1) and an ether-type acetic acid surfactant represented by the formula: $R^3$—Z—$(CH_2CH_2O)_l$—$CH_2CO_2X$ (wherein $R^3$ is a linear or branched alkyl group having 5 to 21 carbon atoms or a linear or branched alkenyl group having 5 to 21 carbon atoms, Z is a group represented by the formula: —O— or a group represented by the formula: —CONH—, X is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total or a protonated basic amino acid, and l is a number of 2 to 15) (8);
iv) a cleanser composition comprising the glycine derivative represented by the above formula (1) and a fatty acid amide derivative represented by the formula:

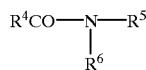

(wherein $R^4$ is a linear or branched alkyl group having 7 to 21 carbon atoms, and $R^5$ and $R^6$ are the same or different from each other and each independently is a hydrogen atom, an alkyl group having 1 to 3 carbon atoms, a hydroxyalkyl group having 1 to 3 carbon atoms or a group represented by the formula: —$(C_2H_4O)_kH$ (wherein k is a number of 2 to 4) (9); and
v) a cleanser composition comprising the glycine derivative represented by the above formula (2).

Among cleanser compositions according to the present invention, those having a pH of 4 to 6.5 are preferable.

Further, the present invention provides a method of washing skin or hair which comprises contacting the skin or hair with the cleanser composition of the present invention described above, and an use of the cleanser composition of the present invention described above for the washing of skin or hair.

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
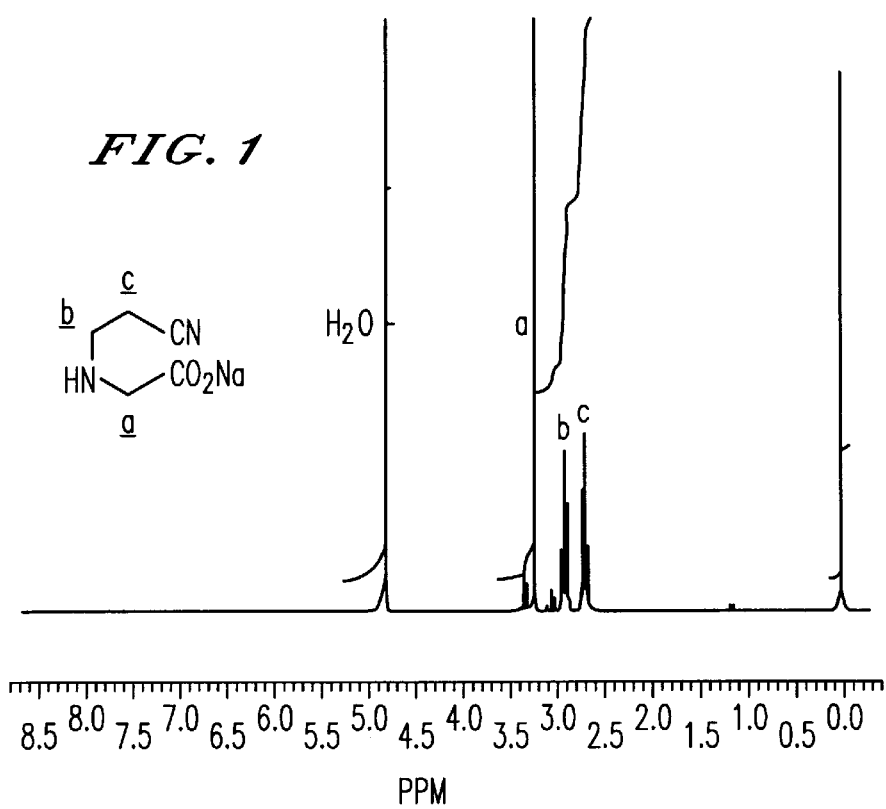
FIG. 1 is the $^1$H-NMR spectrum of the sodium N-cyanoethylglycinate obtained in Example 1.

In the above-mentioned formulas (1) and (2), R is a linear or branched alkyl group having 11 to 13 carbon atoms, a linear or branched alkenyl group having 11 to 13 carbon atoms, or a linear or branched hydroxyalkyl group having 11 to 13 carbon atoms. Specific examples thereof include n-undecyl group, n-dodecyl group, n-tridecyl group and hydroxyundecyl group. Among them, surfactants wherein R is a linear or branched alkyl group having 11 to 13 carbon atoms and other surfactants wherein R is a linear or branched alkenyl group having 11 to 13 carbon atoms are preferred from the viewpoint of foaming power, and those wherein R is a linear alkyl group having 11 to 13 carbon atoms are especially preferred. When the surfactant represented by the above-mentioned formula (1) or (2) is a mixture of compounds which are different from each other only with respect to the carbon atom number of the acyl group, those having an average carbon atom number, which is calculated from the carbon atom numbers of R's of the compounds described above, of from 11 to 13 is included in the scope of the surfactant of the present invention.

In the formulas (1), (2), (3) and (4), $M_1$ and $M_2$ are the same or different from each other and each independently is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total or a protonated basic amino acid. The scope of the protonated basic amino acid includes protonated basic amino acids and inorganic salts thereof. Specific examples of the $M_1$ and $M_2$ include a hydrogen atom, a sodium atom, a potassium atom, ½ (an magnesium atom), ½ (an calcium atom), an ammonium group, a monoethanolammonium group, a diethanolammonium group, a triethanolammonium group, a protonated glutamine, a protonated arginine, a protonated histidine and a protonated lysine. Of these, a hydrogen atom, a sodium atom, a potassium atom, ½ (an magnesium atom), an ammonium group, a monoethanolammonium group, a diethanolammonium group and a triethanolammonium group are preferred. A hydrogen atom, a sodium atom, a potassium atom and an ammonium group are especially preferred.

The following compounds and salts thereof may be mentioned as specific examples of the glycine derivatives represented by the above formula (1) according to the present invention.

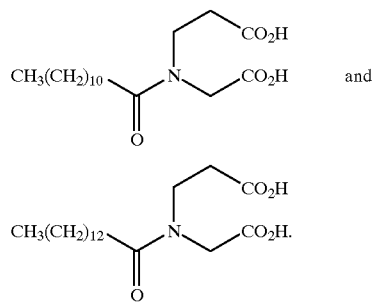

The glycine derivative of the present invention represented by the above general formula (1) (hereinafter referred to simply as "glycine derivative (1)") can be synthesized via the following synthetic route.

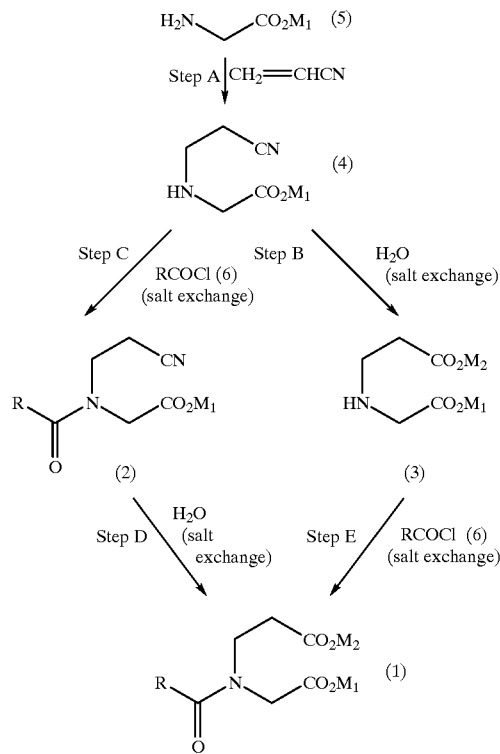

wherein R, $M_1$ and $M_2$ are each as defined above.

That is, the glycine derivative (1) of the present invention can easily be produced through the following steps A, C and D or steps A, B and E conducted in this order.

Step A

This step comprises reacting glycine or a salt thereof represented by the formula (5):

wherein $M_1$ is as defined above, (hereinafter referred to simply as "glycine or its salt (5)") with acrylonitrile to give a glycine derivative represented by the formula (4):

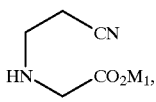

(4)

wherein $M_1$ is as defined above, (hereinafter referred to simply as "glycine derivative (4)").

Step B

This step comprises hydrolyzing the cyano group of the glycine derivative (4), optionally followed by salt exchange to give a glycine derivative represented by the formula (3):

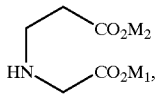

(3)

wherein $M_1$ and $M_2$ are each as defined above, (hereinafter referred to simply as "glycine derivative (3)").

Step C

This step comprises reacting the glycine derivative (4) with an acid chloride represented by the formula (6):

RCOCl (6), wherein R is as defined above, (hereinafter referred to simply as "acid chloride (6)"), optionally followed by salt exchange to give a glycine derivative represented by the formula (2):

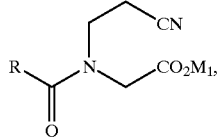

(2)

wherein R and $M_1$ are each as defined above, (hereinafter referred to simply as "glycine derivative (2)").

It seems that the production of the compound represented by the formula:

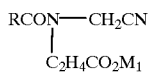

(wherein R and $M_1$ are each as defined above), which dissimilar to the glycine derivative (2) in view of their chemical structures, on an industrial scale is difficult.

Step D

This step comprises hydrolyzing the cyano group of the glycine derivative (2), optionally followed by salt exchange to give the glycine derivative (1).

Step E

This step comprises reacting the glycine derivative (3) with an acid chloride (6), optionally followed by salt exchange to give the glycine derivative (1).

Each of the above steps will be described in detail below.

Step A

This step is one in which the glycine or its salt (5) is reacted with acrylonitrile to thereby obtain the glycine derivative (4).

The glycine or its salt and acrylonitrile as the starting materials may be those which are produced by the known processes, or those which are commercially available. If necessary, the starting materials may be purified by recrystallization, distillation or other means before use.

Specific examples of the glycine or its salt (5) include glycine, sodium glycinate, potassium glycinate, lithium glycinate, magnesium glycinate, calcium glycinate and ammonium glycinate. Of them, sodium glycinate, potassium glycinate and ammonium glycinate are especially preferred.

In this step, the glycine derivative (4) can be obtained by reacting 1 equivalent of the glycine or its salt (5) with 0.5 to 10 equivalents, preferably 0.75 to 5 equivalents, of acrylonitrile in water at an appropriate temperature between 10 and 100° C., preferably between 30 and 70° C. for 0.5 to 100 hours, preferably 1 to 3 hours, optionally followed by counter ion exchange with the use of, e.g., an electrodialyzer. When the reaction time is longer than 100 hours, side reactions such as hydrolysis of the cyano group occur unfavorably. In this reaction, it is preferred that acrylonitrile be gradually added to the aqueous solution of the glycine or its salt (5) to obtain an improved yield, because of markedly reduction of the side reactions such as polymerization of acrylonitrile.

The glycine derivative (4) obtained in this step may be used as is in the subsequent step. If desired, however, it may be recrystallized with the use of a solvent such as water, methanol and ethanol to thereby give a highly purified product.

The thus-obtained glycine derivative (4) is also a novel substance.

The following compounds may be mentioned as specific examples of the glycine derivatives (4).

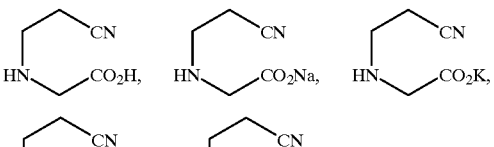

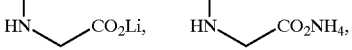

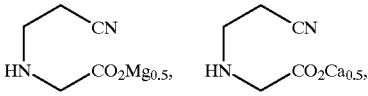

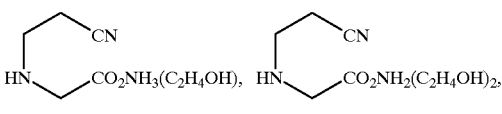

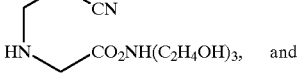

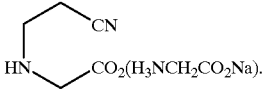

Step B

This step is one in which the cyano group of the glycine derivative (4) obtained in the step A is hydrolyzed preferably in the presence of a basic substance to thereby obtain a glycine derivative (3).

Examples of the basic substances to be used in this step include alkali metal hydroxides and alkaline earth metal hydroxides. Specific examples thereof include sodium hydroxide, potassium hydroxide, magnesium hydroxide, calcium hydroxide and barium hydroxide.

In this step, the glycine derivative (3) can be obtained by reacting the glycine derivative (4) in the presence of 0.1 to 30 equivalents, preferably 0.5 to 15 equivalents, based on 1 equivalent of the glycine derivative (4), of the basic substance in the presence of water and, if necessary, a polar solvent such as methanol, ethanol, isopropanol, acetone, 1,3-propanediol and propylene glycol, at an appropriate temperature between 50 and 100° C., preferably between 70 and 100° C. for 0.5 to 100 hours, optionally followed by counter ion exchange with the use of an electro-dialyzer.

The glycine derivative (3) obtained in this step may be used as is in the subsequent step. If desired, however, it may be recrystallized with the use of a solvent such as water, methanol and ethanol to thereby give a highly purified product.

The thus obtained glycine derivative (3) is also a novel substance.

The following compounds may be mentioned as specified examples of the glycine derivatives (3).

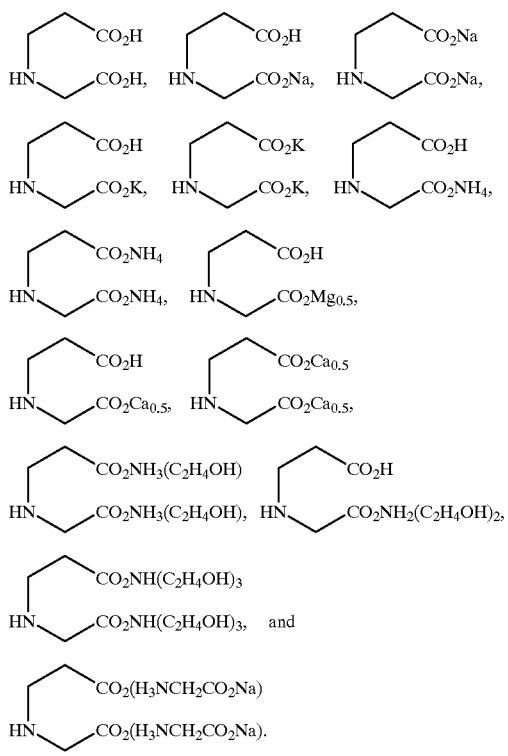

Step C

This step is one in which the glycine derivative (4) obtained in the step A is reacted with an acid chloride (6) preferably in the presence of an alkali substance to thereby obtain a glycine derivative (2).

The acid chloride (6) as one of the starting materials may be one produced by the known process, or commercially available one. If necessary, the starting material may be purified by distillation or other means before use. Specific examples of the acid chlorides (6) include single-composition fatty acid chlorides such as dodecanoyl chloride and tetradecanoyl chloride, and mixed-composition fatty acid chlorides such as cocoyl chloride.

In this step, the glycine derivative (2) can be obtained by reacting 1 equivalent of the glycine derivative (4) with generally 0.8 to 5.0 equivalents, preferably 0.9 to 1.3 equivalents, of the acid chloride (6) in the presence of water and, if necessary, a polar solvent such as methanol, ethanol, isopropanol, acetone, 1,3-propanediol and propylene glycol at an appropriate temperature between 0 and 100° C., preferably between 10 and 50° C. for 0.5 to 100 hours, optionally followed by counter ion exchange with the use of an electrodialyzer.

When the amount of the employed acid chloride (6) is below the above range, unfavorably the glycine derivative (4) remains unreacted in the reaction mixture in large proportion. On the other hand, when it is above this range, a large amount of fatty acids are produced as by-products from unreacted acid chloride (6).

In this step, it is preferred that an alkali substance be added to the reaction system so as to maintain the pH of the system on the alkaline side, preferably to maintain the pH in the range of 9.0 to 11.0 for securing the reactivity by suppressing the decomposition of the acid chloride (6). When the pH of the reaction system is below the above range, the hydrochloric acid produced as a by-product in accordance with the proceeding of the reaction reacts with unreacted glycine derivative (4) to form a salt, so that the reaction does not satisfactorily proceed. On the other hand, when the pH is above this range, the decomposition of the acid chloride (6) is promoted to produce fatty acids as by-products in large proportions.

Specific examples of the alkali substances to be employed include inorganic bases such as sodium hydroxide, potassium hydroxide, calcium hydroxide, barium hydroxide and sodium carbonate, and organic bases such as triethylamine, pyridine and 4-dimethyl-amino pyridine. Of these, sodium hydroxide and potassium hydroxide are especially practical. These alkali substances are used in amounts such that the pH of the system can be maintained within the above range.

The glycine derivative (2) obtained in this step may be used as is in the subsequent step. If desired, however, it may be recrystallized with the use of a solvent such as water, methanol and ethanol. Alternatively, the glycine derivative (2) may be purified by treating the same with a strong acid such as hydrochloric acid and sulfuric acid to thereby obtain a glycine derivative (2) in acidic form, then recrystallizing this acidic derivative from a solvent such as acetone, hexane, petroleum ether, methanol, ethanol and butanol, and thereafter neutralizing it with a suitable neutralizer to thereby give a glycine derivative (2). Thus, highly purified glycine derivative (2) can be obtained.

The thus-obtained glycine derivative (2) is also a novel substance.

The following compounds or salts thereof may be mentioned as specific examples of the glycine derivatives (2).

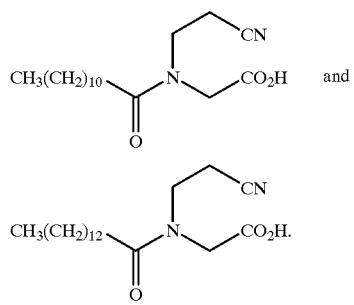

Step D

This step is one in which the cyano group of the glycine derivative (2) obtained in the step C is hydrolyzed preferably in the presence of a basic substance to thereby obtain a glycine derivative (1).

Examples of the basic substances to be used in this step include alkali metal hydroxides and alkaline earth metal hydroxides. Specific examples thereof include sodium hydroxide, potassium hydroxide, magnesium hydroxide, calcium hydroxide and barium hydroxide.

In this step, the glycine derivative (1) can be obtained by reacting the glycine derivative (2) in the presence of 0.1 to 30 equivalents, preferably 0.5 to 15 equivalents, based on 1 equivalent of the glycine derivative (2), of the basic substance in the presence of water and, if necessary, a polar solvent such as methanol, ethanol, isopropanol, acetone, 1,3-propanediol and propylene glycol at an appropriate temperature between 50 and 100° C., preferably between 70 and 100° C. for 0.5 to 100 hours, optionally followed by counter ion exchange with the use of an electrodialyzer.

The glycine derivative (1) obtained in this step may be used as is as a component of, for example, a cleanser composition. If desired, however, it may be recrystallized with the use of a solvent such as water, methanol and ethanol. Alternatively, the glycine derivative (1) may be purified by treating the same with a strong acid such as hydrochloric acid and sulfuric acid to thereby obtain a glycine derivative (1) in acidic form, then recrystallizing this acidic derivative from a solvent such as acetone, hexane, petroleum ether, methanol, ethanol and butanol, and thereafter neutralizing it with a suitable neutralizer to thereby give a glycine derivative (1). Thus, highly purified glycine derivative (1) can be obtained.

Step E

This step is one in which the glycine derivative (3) obtained in the step B is reacted with an acid chloride (6) preferably in the presence of an alkali substance to thereby obtain a glycine derivative (1).

The acid chloride (6) as one of the starting materials is the same one as that used in the above step C.

In this step, the glycine derivative (1) can be obtained by reacting 1 equivalent of the glycine derivative (3) with generally 0.8 to 5.0 equivalents, preferably 0.9 to 1.3 equivalents, of the acid chloride (6) in the presence of water and, if necessary, a polar solvent such as methanol, ethanol, isopropanol, acetone, 1,3-propanediol and propylene glycol at an appropriate temperature between 0 and 100° C., preferably between 10 and 50° C. for 0.5 to 100 hours, optionally followed by counter ion exchange with the use of an electrodialyzer.

When the amount of the employed acid chloride (6) is below the above range, unfavorably the glycine derivative (3) remains unreacted in the reaction mixture in large proportion. On the other hand, when it is above this range, a large amount of fatty acids are produced as by-products from unreacted acid chloride (6).

In this step, it is preferred that an alkali substance be added to the reaction system so as to maintain the pH of the system on the alkaline side, preferably to maintain the pH in the range of 9.0 to 11.0 for securing the reactivity by suppressing the decomposition of the acid chloride (6). When the pH of the reaction system is below the above range, the hydrochloric acid produced as a by-product in accordance with the proceeding of the reaction reacts with uunreacted glycine derivative (3) to form a salt, so that the reaction does not satisfactorily proceed. On the other hand, when the pH is above this range, the decomposition of the acid chloride (6) is promoted to produce fatty acids as by-products in large proportions.

Specific examples of the alkali substances to be used in this step include inorganic bases such as sodium hydroxide, potassium hydroxide, calcium hydroxide, barium hydroxide and sodium carbonate, and organic bases such as triethylamine, pyridine and 4-dimethylaminopyridine. Of these, sodium hydroxide and potassium hydroxide are especially practical. These alkali substances are used in amounts such that the pH of the system can be maintained within the above range.

The glycine derivative (1) obtained in this step may be used as is as a component of, for example, a cleanser composition. If desired, however, it may be subjected to the same aftertreatment as the one described in step D to thereby obtain a product of increased purity.

The glycine derivatives (1) and (2) according to the present invention are novel surfactants which are excellent in not only safety but also foaming power, detergency, comfort in use and general purpose availability and are suitable for use as a component of a cleanser composition for, e.g., hair, body or tableware.

The cleanser composition of the present invention contains the glycine derivative (1) or (2) as an essential component. The cleanser composition of the present invention may contain one of the glycine derivatives (1), or two or more of them. The cleanser composition of the present invention may contain one of the glycine derivatives (2), or two or more of them. The amount of the glycine derivative (1) or (2) contained is preferably 0.1 to 99% by weight, still more preferably 0.1 to 70% by weight, based on the total weight of the composition. Typically, the compositions will also contain water.

The cleanser composition containing the glycine derivative (1) according to the present invention may further contain a sugar surfactant represented by the formula: $R^1$—$(OR^2)_m$—$G_n$ (wherein $R^1$ is a linear or branched alkyl group having 8 to 18 carbon atoms, a linear or branched alkenyl group having 8 to 18 carbon atoms, or a substituted phenyl group having a linear or branched alkyl group of 8 to 18 carbon atoms, $R^2$ is an alkylene group having 2 to 4 carbon atoms, G is a residue derived from a reducing sugar having 5 to 6 carbon atoms, m is a number of 0 to 10 and n is a number of 1 to 10) (7); an ether-type acetic acid surfactant represented by the following formula: $R^3$—Z—$(CH_2CH_2O)_1$—$CH_2CO_2X$ (wherein $R^3$ is a linear or branched alkyl group having 5 to 21 carbon atoms or a linear or branched alkenyl group having 5 to 21 carbon atoms, Z is a group represented by the formula: —O— or a group represented by the formula: —CONH—, X is a hydrogen atom, an alkali metal atom, ½ (an alkaline earth metal atom), an ammonium group, a monoalkanol-ammonium group having 1 to 22 carbon atoms, a dialkanolammonium group having 2 to 22 carbon atoms in total, a trialkanolammonium group having 3 to 22 carbon atoms in total or a protonated basic amino acid, and l is a number of 2 to 15) (8); or a fatty acid amide derivative represented by the following formula:

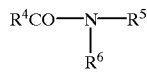

(wherein $R^4$ is a linear or branched alkyl group having 7 to 21 carbon atoms, and $R^5$ and $R^6$ are the same or different from each other and each independently is a hydrogen atom, an alkyl group having 1 to 3 carbon atoms, a hydroxyalkyl group having 1 to 3 carbon atoms or a a group represented by the formula: —$(C_2H_4O)_kH$ (wherein k is a number of 2 to 4) (9).

In the above-mentioned formula (7), $R^1$ is a linear or branched alkyl group having 8 to 18 carbon atoms, a linear or branched alkenyl group having 8 to 18 carbon atoms, or a substituted phenyl group having a linear or branched alkyl group of 8 to 18 carbon atoms. An alkyl group having 10 to 14 carbon atoms is preferable, and examples thereof include decyl group, dodecyl group and tetradecyl group. $R^2$ is an alkylene group having 2 to 4 carbon atoms. Ethylene group or propylene group is preferable as $R^2$.

G is a residue derived from a reducing sugar having 5 to 6 carbon atoms. Its structure is dependent on the chemical structure of the monosaccharide or polysaccharide used as the starting material. Examples of the starting material of the sugar surfactant represented by the above formula (7) (hereinafter referred to "sugar surfactant (7)"), which provides the residue represented by G, include monosaccharides such as glucose, galactose, fructose, xylose, mannose, lyxose and arabinose, polysaccharides such as maltose, xylobiose, isomaltose, cellobiose, gentiobiose, lactose, sucrose, nigerose, turanose, raffinose, gentianose and melezitose, and mixtures thereof. Of these, glucose, galactose and fructose are particularly preferred.

In the formula (7), m is a number of 0 to 10, preferably 0 to 2. In the formula (7), n is an average sugar polymerization degree, being a number of 1 to 10, which is preferably selected taking the properties attributed to the functional group, $R^1$, into account. For example, when $R^1$ is a hydrophobic group having 8 to 11 carbon atoms, n is preferably in the range of 1 to 1.4; and when $R^1$ is a hydrophobic group having 12 to 14 carbon atoms, n is preferably in the range of 1.5 to 4.0. The average sugar polymerization degree n is determined by the proton-NMR method.

Among sugar surfactants (7), alkylpolyglucosides wherein m is 0 and G is a residue derived from glucose, i.e., those represented by the formula: $R^1$—$G_n$, are particularly preferred.

In the cleanser composition of the present invention, the sugar surfactant (7) may be used individually, or a plurality thereof may be used in combination.

In the cleanser composition comprising the glycine derivative (1) and the sugar surfactant (7) according to the present invention, the amount of the glycine derivative (1), which depends on, for example, the form of the cleanser composition, is preferably from 2 to 60% by weight, especially preferably from 5 to 50% by weight, based on the total weight of the composition. Such cleanser compositions exhibit excellent foaming and give clean feeling after washing. The amount of the sugar surfactant (7), which depends on, for example, the form of the cleanser composition, is preferably from 2 to 60% by weight, especially preferably from 5 to 50% by weight, based on the total weight of the composition. Such cleanser compositions exhibit excellent foaming and are also improved in the storage stability at low temperatures.

The weight ratio of the glycine derivative (1) to the sugar surfactant (7) is preferably from 1/30 to 30/1, still more preferably from 1/10 to 10/1, and especially preferably from 1/1 to 4/1.

In the above-mentioned formula (8), $R^3$ is a linear or branched alkyl group having 5 to 21 carbon atoms or a linear or branched alkenyl group having 5 to 21 carbon atoms. A linear or branched alkyl group having 11 to 15 carbon atoms and a linear or branched alkenyl group having 11 to 15 carbon atoms are preferable. In the formula (8), 1, which represents an average number of oxyethylene groups, is a number of 2 to 15, of which a number of 2 to 8 is preferred. The ether-type acetic acid surfactant represented by the above-mentioned formula (8) wherein 1 exceeds 15 is poor in foaming power. On the other hands, the one wherein 1 is less than 2 cannot give a composition containing it in a high concentration.

Preferred examples of the ether-type acetic acid surfactants represented by the formula (8) (hereinafter referred to "ether-type acetic acid surfactant (8)") include polyoxyethylene (2) lauryl ether acetic acid ($R^3$=$C_{12}H_{25}$, Z=—O—, 1=2, and X=H in formula (8)); polyoxyethylene (8) myristyl ether acetic acid ($R^3$=$C_{14}H_{28}$, Z=—O—, 1=8, and x=H in formula (8)); mono(polyoxyethylene (3) lauramide ether)methane carboxylic acid ($R^3$=$C_{11}H_{23}$, Z=—CONH—, 1=3, and X=H in formula (8)); mono (polyoxyethylene (6) lauramide ether)methane carboxylic acid ($R^3$=$C_{11}H_{23}$, Z=—CONH—, 1=6, and X=H in formula (8)); mono(polyoxyethylene (2) lauramide ether) methane carboxylic acid ($R^3$=$C_{11}H_{23}$, Z=—CONH—, 1=2, and X=H in formula (8)); and salts thereof. Those having a degree of neutralization of from 60 to 120% are preferable. It is preferred that the counter ion, X, be an alkali metal, especially potassium atom or sodium atom. And it is preferred that the counter ion, X, be identical with $M_1$ and/or $M_2$ of the glycine derivative (1) simultaneously used.

In the cleanser composition of the present invention, the ether-type acetic acid surfactant (8) may be used individually, or a plurality thereof may be used in combination.

In the cleanser composition comprising the glycine derivative (1) and the ether-type acetic acid surfactant (8) according to the present invention, the amount of the glycine derivative (1), which depends on, for example, the form of the cleanser composition, is preferably from 2 to 60% by weight, especially preferably from 5 to 50% by weight, based on the total weight of the composition. Such cleanser compositions exhibit excellent foaming and give a clean feeling after washing. The amount of the ether-type acetic acid surfactant (8), which depends on, for example, the form of the cleanser composition, is preferably from 2 to 60% by weight, especially preferably from 5 to 50% by weight, based on the total weight of the composition. Such cleanser compositions exhibit excellent foaming and are also improved in storage stability at low temperatures.

The weight ratio of the glycine derivative (1) to the ether-type acetic acid surfactant (8) is preferably from 100/1 to 1/2, still more preferably from 50/1 to 1/1, and especially preferably from 10/1 to 2/1.

In the above-mentioned formula (9), $R^4$ is a linear or branched alkyl group having 7 to 21 carbon atoms. A linear or branched alkyl group having 12 to 18 carbon atoms, e.g., dodecyl group, tridecyl group, tetradecyl group, pentadecyl group or heptadecyl group, is especially preferred. With respect to $R^5$ and $R^6$, it is preferred that both are hydroxyalkyl groups, especially hydroxyethyl groups, or that one is a hydroxyalkyl group, especially a hydroxyethyl group while the other is a hydrogen atom.

Preferred examples of the fatty acid amide derivatives represented by the above-mentioned formula (9) (hereinafter referred to "fatty acid amide derivative (9)") include lauroyl monoethanolamide, lauroyl diethanolamide, coconut fatty acid monoethanolamide, coconut fatty acid diethanolamide, lauroyl monoisopropanolamide and coconut fatty acid monoisopropanolamide.

In the cleanser composition of the present invention, the fatty acid amide derivative (9) may be used individually, or a plurality thereof may be used in combination.

In the cleanser composition comprising the glycine derivative (1) and the fatty acid amide derivative (9) according to the present invention, the amount of the glycine derivative (1), which depends on, for example, the form of the cleanser composition, is preferably from 2 to 60% by weight, especially preferably from 5 to 50% by weight, based on the total weight of the composition. Such cleanser compositions exhibit excellent foaming and give a clean feeling after washing. The amount of the fatty acid amide derivative (9), which depends on, for example, the form of the cleanser composition, is preferably from 0.1 to 10% by weight, especially preferably from 1 to 5% by weight, based on the total weight of the composition. Such cleanser compositions give a very creamy foam.

The weight ratio of the glycine derivative (1) to the fatty acid amide derivative (9) is preferably from 100/1 to 2/1, especially 50/1 to 5/1. The sum of the glycine derivative (1) and the fatty acid amide derivative (9), which depends on, for example, the form of the cleanser composition, is preferably, based on the total weight of the composition, from 5 to 50% by weight in the case of a liquid cleanser composition, from 15 to 70% by weight in the case of a pasty cleanser composition, and from 40 to 95% by weight in the case of a solid cleanser composition.

The cleanser composition of the present invention may contain other conventional components of cleanser compositions for the hair, body, and tableware as long as the presence of such components is not detrimental to the effect of the present invention. Examples of the such other components include anionic surfactants (such as alkyl sulfate salts, polyoxyethylene alkyl ether sulfate salts, alkylbenzene sulfonates, higher fatty acid salts, α-olefin sulfonates, alkylsulfonates, N-alkylcarbamylalkanol sulfate salts, N-alkanoylethanolamide sulfate salts, fatty acid glyceride sulfates, alkyl glyceryl ether sulfates, taurinate surfactants, sarcosinate surfactants, isethionate surfactants and N-acylated acidic amino acid surfactants), amphoteric surfactants (such as alkylbetaine surfactants, carbamylpropylbetaine surfactants, imidazolinium betaine surfactants, sulfobetaine surfactants, phosphobetaine surfactants and amino acid surfactants, e.g., sodium laurylamino-propionate), nonionic surfactants (such as polyoxyethylene alkyl ethers, polyoxyethylene fatty acid esters, monofatty acid esters of glycerol, fatty acid sorbitan esters and alkylpolyglycosides), cationic surfactants (such as alkyltrimethylammonium chlorides, dialkyldimethylammonium chlorides and ethyl (lanonlin fatty acid) aminopropylethyldimethylammonium sulfate), humectants (such as glycerol, propylene glycol and ethylene glycol), thickeners, disinfectants, antiseptics, emulsifiers, polymers (such as carboxyethylcellulose, hydroxyethylcellulose and cationized cellulose) and fragrances.

When the cleanser composition of the present invention contains the glycine derivative (1), and the sugar surfactant (7), the ether-type acetic acid surfactant (8) or the fatty acid amide derivative (9) as essential components, the composition may contain, as long as the presence of such a surfactant is not detrimental to the effect of the present invention, a surfactant other than those described above, for example, an anionic surfactant such as an N-acyl-sarcosine salt, an alkyl ether sulfate and a polyoxyethylene alkyl ether sulfate, a nonionic surfactant such as a polyoxyethylene alkyl ether, a sugar ester surfactant and a sugar amide surfactant, or an amphoteric surfactant such as an imidazoline surfactant and a betaine surfactant. Moreover, the cleanser composition may contain, as long as the presence of such components is not detrimental to the effect of the present invention, other conventional components of cleanser compositions, for example, viscosity modifiers such as a carboxyvinyl polymer, methylcellulose, ethanol and a polyoxyethylene glycol distearate, pearling agents, fragrances, coloring matters, ultraviolet absorbers, antioxidants, disinfectants, anti-inflammatory agents or antiseptics.

It is preferred that the pH of an aqueous solution obtained by diluting the cleanser composition of the present invention 10-fold by weight with water be in the range of 4 to 9, especially 4 to 6.5. An acid or a base may be added to the cleanser composition during the preparation thereof, or an equimolar ion exchange of the glycine derivative (1) may be conducted, in order to adjust the pH thereof to a desired value.

The cleanser composition of the present invention may be produced according to conventional procedures. The form of the cleanser composition is not particularly limited and examples of the form include liquid, pasty, creamy, solid and powdery forms. It is especially preferred that the cleanser composition be in the form of a liquid, paste or cream. When a liquid cleanser composition is produced, water is preferably employed as a liquid medium. The amount of water contained in the liquid cleanser composition is preferably from 50 to 90% by weight, based on the total weight of the composition.

The cleanser composition of the present invention exhibits excellent foaming and foam stability in washing, exhibits excellent foam breaking and is free from sliminess and stickiness during rinsing, has reduced irritancy to the skin and is excellent in the storage stability at low temperatures.

The cleanser composition of the present invention may be used to wash the hair and/or body as well as articles such as tableware. In such methods, a composition according to the present invention is applied to the hair, skin or article for a sufficient time to effect cleaning of the hair, skin or article, and then rinsed from the hair, skin or article with water. The cleanser composition of the present invention is suitable as one for body such as skin and hair, especially as a skin cleanser composition. Although it is preferred that the hair or skin be human, the present compositions may also be used to wash the hair or skin of animals such as cats, dogs, etc.

Other features of the invention will become apparent in the course of the following descriptions of exemplary embodiments which are given for illustration of the invention and are not intended to be limiting thereof.

EXAMPLES

Example 1

Sodium N-cyanoethylglycinate 150.77 g (2.0084 mol) of glycine and 100 ml of water were fed into a 1Λ four-necked flask equipped with a stirrer, a thermometer, and a dropping funnel. 200 ml of an aqueous solution of 80.46 g (2.0115 mol) of NaOH was added thereto while stirring to thereby give an aqueous sodium glycinate solution. Then, 106.7 g (2.0109 mol) of acrylonitrile was dropwise added to this solution over a period of about 30 minutes while stirring. During the dropwise addition, the reaction system was maintained at a temperature of from 40 to 70° C. Thereafter, the reaction mixture was stirred at 60° C. for 2 hours to thereby complete the reaction. After the completion of the reaction, the reaction system was cooled to room temperature. Thus, 568 g (yield: 97.8%) of a 51.9% aqueous solution of sodium N-cyanoethylglycinate was obtained. A portion thereof was taken out, dehydrated and dried, thereby obtaining a colorless powder. The powder was subjected to the following analyses. As a result, it was confirmed that the obtained product was a compound represented by the following formula:

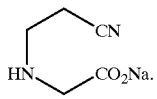

Figure 3:
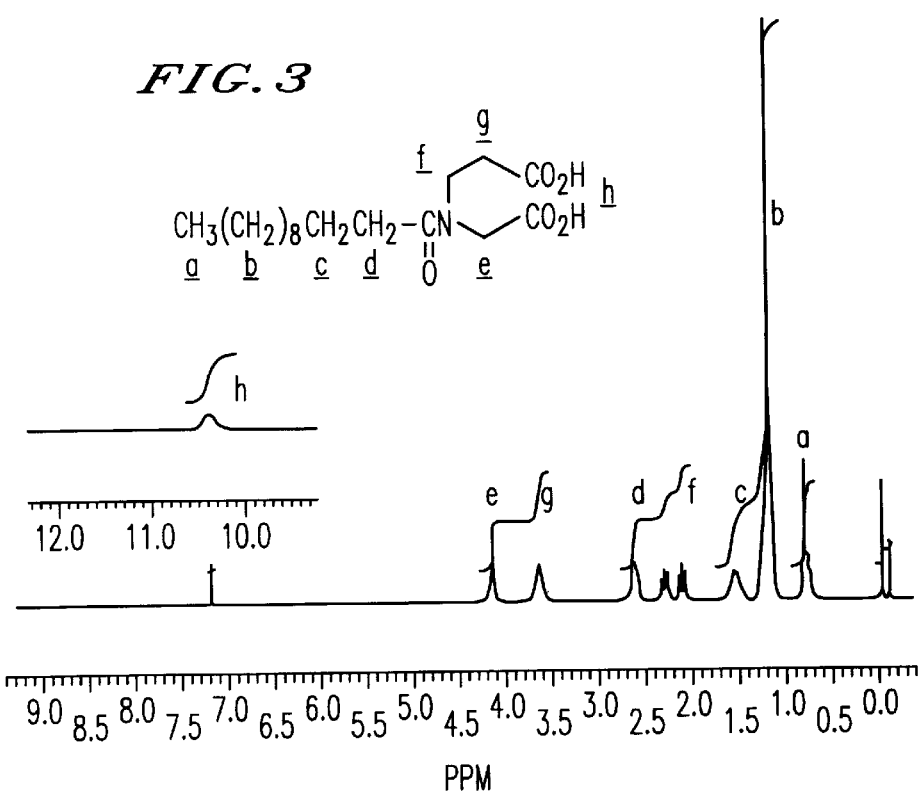
FIG. 3 is the $^1$H-NMR spectrum of the N-carboxy-ethyl-N-dodecanolyglycine obtained in Example 6.

$^1$H-NMR spectrum (200 MHz, D$_2$O): shown in FIG. 1
3.21 (s,2 H), 2.90 (t,2 H), 2.68 (t,2 H) ppm
Elemental analysis (C$_5$H$_7$N$_2$O$_2$Na=150.11)
Calculated (%) C: 40.01, H: 4.70, N: 18.66, O: 21.32
Found (%,) C: 40.01, H: 4.68, N: 18.80, O: 21.41

Example 2
N-Cyanoethyl-N-dodecanoylglycine 222.4 g (0.7689 mol) of the 51.9% aqueous solution of sodium N-cyanoethylglycinate obtained in Example 1 and 50 ml of acetone were fed into a 1a four-necked flask equipped with a stirrer, a thermometer and a dropping funnel, and cooled with ice. Then, 183.9 g (0.8406 mol) of dodecanoyl chloride was dropwise added to this solution over a period of 1 hour while stirring. During the dropwise addition, the reaction system was maintained at pH 9 to 11 by dropwise adding a 40% aqueous solution of NaOH while the temperature was maintained at 10 to 25° C. After the completion of the dropwise addition of the dodecanoyl chloride, the reaction mixture was stirred at room temperature for 2 hours. Thereafter, the pH of the reaction mixture was adjusted to 1.2 with concentrated hydrochloric acid. A water insoluble component in the reaction mixture was extracted with chloroform. The obtained organic phase was concentrated and satisfactorily dried. Thus, 228.99 g (yield: 95.9%) of a colorless powder of N-cyanoethyl-N-dodecanoylglycine represented by the following formula was obtained. The acid value thereof was 189.2 (calculated: 180.73).

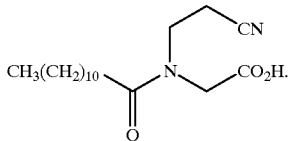

Figure 2:
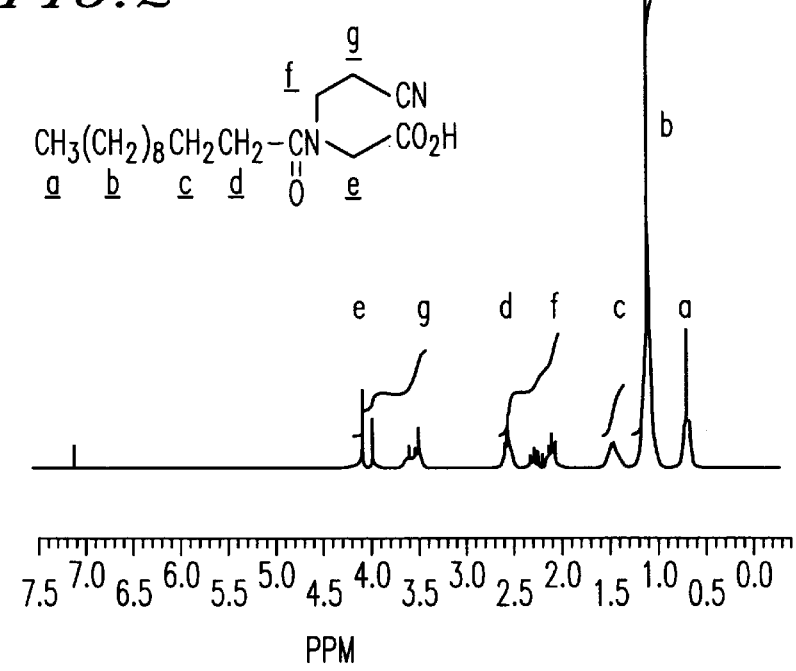
FIG. 2 is the $^1$H-NMR spectrum of the N-cyanoethyl-N-dodecanoylglycine obtained in Example 2.
Figure 4:
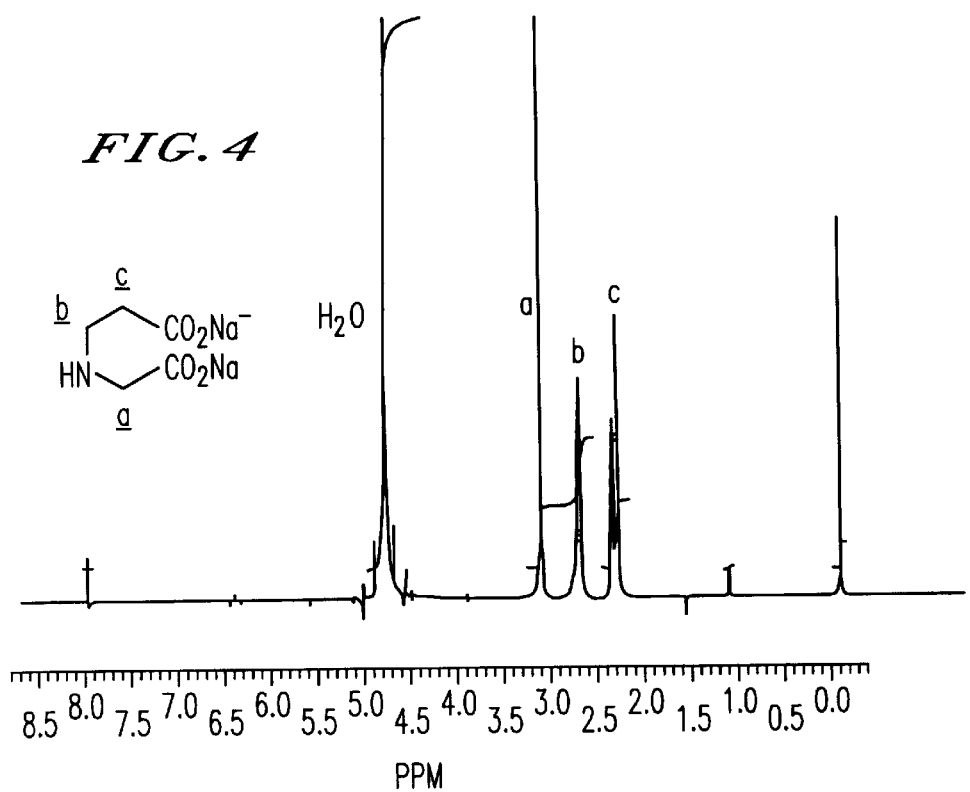
FIG. 4 is the $^1$H-NMR spectrum of the disodium N-carboxyethylglycinate obtained in Example 7.

Infrared absorption spectrum (KBr)
2928 (s), 2856 (s), 2244 (w), 1740 (s), 1606 (s), 1184 (s) cm$^{-1}$ $^1$H-NMR spectrum (200 MHz, CDCl$_3$): shown in FIG. 2
4.20 (s,1 H), 4.11 (s,1 H), 3.72 (t,1 H), 3.63 (t,1 H), 2.68 (t,1 H), 2.66 (t,1 H), 2.42 (t,1 H), 2.25 (t,1 H), 1.61 (m,2 H), 1.26 (b,16 H), 0.86 (t,3 H) ppm
Elemental analysis (C$_{17}$H$_{30}$N$_2$O$_3$=310.44)
Calculated (%) C: 65.77, H: 9.74, N: 9.02, O: 15.46
Found (%) C: 65.63, H: 9.76, N: 8.99, O: 15.53

Example 3
Sodium N-cyanoethyl-N-dodecanoylglycinate

Sodium N-cyanoethylglycinate was acylated with the use of dodecanoyl chlordide and a 48% aqueous solution of NaOH in the same manner as that of Example 2. The pH of the resultant aqueous solution of the reaction mixture was adjusted to 7.0 with concentrated hydrochloric acid. The obtained aqueous solution was desalted with the use of an electrodialyzer to thereby reduce the salt concentration to 2% or below. Thereafter, the water was evaporated off with the use of a rotary evaporator, and the residue was washed with acetone to thereby give sodium N-cyanoethyl-N-dodecanoylglycinate as a colorless powder.

Infrared absorption spectrum (KBr)
2928 (s), 2856 (s), 2260 (w), 1638 (s), 1622 (s), 1560 (w), 1470 (m), 1422 (m), 1400 (m), 1384 (m), 1318 (m), 718 (w) cm$^{-1}$ $^1$H-NMR spectrum (200 MHz, D$_2$O)
4.02 (s,1 H), 3.94 (s,1 H), 3.76 (t,1 H), 3.65 (t,1 H), 2.80 (t,1 H), 2.71 (t,1 H), 2.50 (t,1 H), 2.30 (t,1 H), 1.60 (m,2 H), 1.31 (b,16 H), 0.89 (t,3 H) ppm Example 4
Potassium N-cyanoethyl-N-dodecanoylglycinate A 30% aqueous solution of KOH was gradually added to the N-cyanoethyl-N-dodecanoylglycine obtained in Example 2 to thereby adjust the pH of the system to 6.0. Thus, an aqueous solution of potassium N-cyanoethyl-N-dodecanoylglycinate was obtained. $^1$H-NMR spectrum (200 MHz, D$_2$O) 4.02 (s,1 H), 3.94 (s,1 H), 3.76 (t,1 H), 3.65 (t,1 H), 2.80 (t,1 H), 2.71 (t,1 H), 2.50 (t,1 H), 2.30 (t,1 H), 1.60 (m,2 H), 1.31 (b,16 H), 0.89 (t,3 H) ppm Example 5
Ammonium N-cyanoethyl-N-dodecanovylglycinate 28% aqueous ammonia was gradually added to the N-cyanoethyl-N-dodecanoylglycine obtained in Example 2 to thereby adjust the pH of the system to 6.5. Thus, an aqueous solution of ammonium N-cyanoethyl-N-dodecanoylglycinate was obtained.

$^1$H-NMR spectrum (200 MHz, D$_2$O) 4.02 (s,1 H), 3.94 (s,1 H), 3.76 (t,1 H), 3.65 (t,1 H), 2.80 (t,1 H), 2.71 (t,1 H), 2.50 (t,1 H), 2.30 (t,1 H), 1.60 (m,2 H), 1.31 (b,16 H), 0.89 (t,3 H) ppm Example 6
N-Carboxyethyl-N-dodecanoylglycine 110.18 g (0.3549 mol) of N-cyanoethyl-N-dodecanoylglycine obtained in Example 2 and 200 ml of water were fed into a 1Λ four-necked flask equipped with a stirrer, a thermometer and a cooling tube, and cooled with ice. Then, 200 ml of an aqueous solution of 58.6 g (0.888 mol) of KOH was added thereto while stirring. The resultant solution was stirred at 90° C. for 2 hours. Thereafter, the solution was cooled to room temperature, and the pH thereof was adjusted to 1.5 with concentrated hydrochloric acid. A water insoluble component in the reaction mixture was extracted with chloroform, and the obtained organic phase was concentrated and satisfactorily dried. Thus, 113.71 g (yield: 97.3%) of a colorless powder of N-carboxyethyl-N-dodecanoylglycine represented by the following formula was obtained.

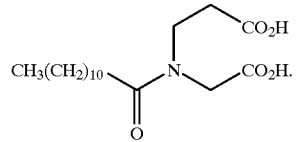

Infrared absorption spectrum (KBr) 3150 (b), 2924 (s), 2860 (s), 1724 (s), 1616 (s), 1478 (s), 1418 (m), 1258 (s), 1188 (s) cm-1

$^1$H-NMR spectrum (200 MHz, CDCl$_3$): shown in FIG. 3
10.4 (b,2 H), 4.19 (s,1 H), 4.17 (s,1 H), 3.67 (dd,2 H), 2.65 (t,2 H), 2.33 (t,1 H), 2.12 (t,1 H), 1.58 (m,2 H), 1.23 (b,16 H), 0.80 (t,3 H) ppm
Mass spectrum (FAB ionization method, negative)
m/z=679 (2 M+Na−2), 328 (M−1), 256 (base), 212
Elemental analysis (C$_{17}$H$_{31}$NO$_5$=329.44)
Calculated (%) C: 61.98, H: 9.48, N: 4.25, O: 24.28
Found (%) C: 62.06, H: 9.48, N: 4.09, O: 24.31

Example 7
Disodium N-carboxyethylglycinate 80.00 g (1.0657 mol) of glycine and 160 ml of an aqueous solution of 42.63 g (1.066 mol) of NaOH were fed into a 2Λ four-necked flask equipped with a stirrer, a thermometer and a dropping funnel, and heated while stirring. Then, 59.38 g (1.119 mol) of acrylonitrile was dropwise added to this solution over a period of about 30 minutes while stirring. During the dropwise addition, the reaction system was maintained at a temperature of from 40 to 60° C. After the completion of the dropwise addition, the reaction mixture was stirred at 60° C. for 1 hour. 300 ml of an aqueous solution of 63.95 g (1.5988 mol) of NaOH was fed into thereto while stirring. Thereafter, the temperature was raised to 80° C., and the reaction solution was stirred for 2 hours. During this period, nitrogen gas was blown into the reaction solution, thereby continuously eliminating generated ammonia gas from the system. After the completion of the reaction, the reaction system was cooled to room temperature. Thus, disodium N-carboxyethylglycinate represented by the following formula was obtained. A portion thereof was taken out, dehydrated and dried, thereby obtaining a colorless powder.

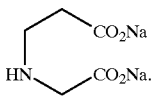

Infrared absorption spectrum (KBr) 3420 (b), 2952 (w), 2820 (w), 1584 (s), 1424 (s) cm$^{-1}$ $^1$H-NMR spectrum (200 MHz, D$_2$O): shown in FIG. 4 3.15 (s,2 H), 2.72 (t,2 H), 2.37 (t,2 H) ppm

Example 8
N-Carboxyethyl-N-dodecanoylglycine 150 ml of acetone was added to the aqueous solution of disodium N-carboxyethylglycinate obtained in Example 7 while continuously stirring. Then, 228.29 g (1.0435 mol) of dodecanoyl chloride was dropwise added to this solution over a period of 1.5 hours while stirring. During this period, the reaction system was maintained at a pH of from 9 to 11 by dropwise adding a 40% aqueous solution of NaOH while the temperature was maintained at 10 to 25° C. After the completion of the dropwise addition, the reaction mixture was stirred at room temperature for 2 hours. Thereafter, the pH of the reaction mixture was adjusted to 1.2 with concentrated hydrochloric acid. A formed white precipitate was separated by filtration, washed with water and dried to thereby give 324.71 g (yield from glycine: 92.5%) of a white powder of N-carboxyethyl-N-dodecanoylglycine. The infrared absorption spectrum, $^1$H-NMR spectrum, mass spectrum, and results of elemental analysis thereof were the same as those obtained in Example 6.

Example 9
Sodium N-carboxyethyl-N-dodecanoylglycinate

Disodium N-carboxyethylglycinate was acylated with the use of dodecanoyl chloride and a 48% aqueous solution of NAOH in the same manner as that in Example 8. The pH of the resultant aqueous solution of the reaction mixture was adjusted to 7.0 with concentrated hydrochloric acid. The obtained aqueous solution was desalted with the use of an electrodialyzer to thereby reduce the salt concentration to 2% or below. Thereafter, the water was evaporated off with the use of a rotary evaporator, and the residue was washed with acetone to thereby give sodium N-carboxyethyl-N-dodecanoylglycinate (the term, "sodium" includes monosodium, disodium, and a mixture of monosodium and disodium, herein) as a colorless powder.

Infrared absorption spectrum (KBr) 2928 (s), 2856 (s), 1650 (s), 1630 (s), 1606 (s), 1588 (s), 1482 (m), 1464 (s), 1442 (s), 1422 (s), 1406 (s), 1360 (m), 1306 (m) cm$^{-1}$ $^1$H-NMR spectrum (200 MHz, D$_2$O) 3.96 (s,1 H), 3.89 (s,1 H), 3.59 (m,2 H), 2.44 (m,3 H), 2.28 (t,lH), 1.57 (m,2 H), 1.30 (b,16 H), 0.90 (t,3 H) ppm

Example 10
Potassium N-carboxyethyl-N-dodecanoylglycinate 80.50 g (1.0723 mol) of glycine and 150 ml of an aqueous solution of 60.20 g (1.073 mol) of KOH were fed into a 2Λ four-necked flask equipped with a stirrer, a thermometer and a dropping funnel, and heated while stirring. Then, 56.90 g (1.072 mol) of acrylonitrile was dropwise added to this solution over a period of about 30 minutes while stirring. During this period, the reaction system was maintained at a temperature of from 45 to 55° C. After the completion of the dropwise addition, the reaction mixture was stirred at 55° C. for 1 hour, and the temperature was lowered to room temperature. Subsequently, 120 ml of water and 90 ml of acetone were added to the reaction solution thus obtained, and then 234.50 g (1.0719 mol) of dodecanoyl chloride was dropwise added thereto over a period of 1 hour while stirring. During this period, the reaction system was maintained at a pH of from 9 to 11 by dropwise adding a 30% aqueous solution of KOH while the temperature was maintained at 5 to 25° C. After the completion of the dropwise addition of the dodecanoyl chloride, the resulting reaction mixture was stirred at room temperature for 2 hours. Then, a 30% aqueous solution of KOH was further added in an amount such that the sum of the amount of KOH and that previously added for pH adjustment was 150.00 g (2.673 mol). Thereafter, the reaction solution thus obtained was stirred at 80° C. for 2 hours. During this period, nitrogen gas was blown into the reaction solution, thereby continuously eliminating generated ammonia gas from the system. Thereafter, the reaction solution was cooled to room temperature, and then the pH of the system was adjusted to 6.0 with concentrated hydrochloric acid. The obtained aqueous solution was desalted with the use of an electrodialyzer. Thus, potassium N-carboxyethyl-N-dodecanoylglycinate (the term, "potassium" includes monopotassium, dipotassium, and a mixture of monopotassium and dipotassium, herein) was obtained in the form of an aqueous solution.

$^1$H-NMR spectrum (200 MHz, D$_2$O) 3.96 (s,1 H), 3.89 (s,1 H), 3.59 (m,2 H), 2.44 (m,3 H), 2.28 (t,1 H), 1.57 (m,2 H), 1.30 (b,16 H), 0.90 (t,3 H) ppm

Example 11
Magnesium N-carboxyethyl-N-dodecanoylglycinate

To the N-carboxyethyl-N-dodecanoylglycine obtained in Example 8, distilled water was added in a volume of three times that of the N-carboxyethyl-N-dodecanoylglycine. Then, the resultant suspension was heated to 40° C. while stirring. Powdery Mg(OH)$_2$ was gradually added thereto while stirring to thereby adjust the pH of the system to 6.0. Thus, an aqueous solution of magnesium N-carboxyethyl-N-dodecanoyl-glycinate (the term, "magnesium" includes ½ (magnesium), magnesium, and a mixture of ½ (magnesium) and magnesium, herein)) was obtained.

$^1$H-NMR spectrum (200 MHz, D$_2$O) 3.96 (s,1 H), 3.89 (s,1 H), 3.59 (m,2 H), 2.44 (m,3 H), 2.28 (t,1 H), 1.57 (m,2 H), 1.30 (b,16 H), 0.90 (t,3 H) ppm

Example 12
Ammonium N-carboxyethyl-N-dodecanoylglycinate

28% aqueous ammonia was gradually added to the N-carboxyethyl-N-dodecanoylglycine obtained in Example 8 to thereby adjust the pH of the system to 6.5. Thus, an aqueous solution of ammonium N-carboxyethyl-N-dodecanoylglycinate (the term, "ammonium" includes monoammonium, diammonium, and a mixture of monoammonium and diammonium, herein) was obtained.

$^1$H-NMR spectrum (200 MHz, $D_2O$) 3.96 (s,1 H), 3.89 (s,1 H), 3.59 (m,2 H), 2.44 (m,3 H), 2.28 (t,1 H), 1.57 (m,2 H), 1.30 (b,16 H), 0.90 (t,3 H) ppm

Example 13
N-Carboxyethyl-N-tetradecanoylglycine 50.01 g (0.6662 mol) of glycine and 100 ml of an aqueous solution of 26.68 g (0.667 mol) of NaOH were fed into a 2Λ four-necked flask equipped with a stirrer, a thermometer and a dropping funnel, and heated while stirring. Then, 37.23 g (0.7017 mol) of acrylonitrile was dropwise added to this solution over a period of about 20 minutes while stirring. During the dropwise addition, the reaction system was maintained at a temperature of from 40 to 50° C. After the completion of the dropwise addition, the reaction mixture was stirred at 50° C. for 1 hour, and the temperature was lowered to room temperature. Subsequently, 200 ml of water and 120 ml of acetone were added to the reaction solution thus obtained, and 164.91 g (0.6681 mol) of tetradecanoyl chloride was dropwise added thereto over a period of 1 hour while stirring. During the dropwise addition of the tetradecanoyl chloride, the reaction system was maintained at a pH of from 9 to 11 by dropwise adding a 30% aqueous solution of NaOH while the temperature was maintained at 5 to 30° C. After the completion of the dropwise addition, the reaction mixture was stirred at room temperature for 1 hour. Then, 50 ml of ethanol and a 30% aqueous solution of NaOH were added thereto. The 30% aqueous solution of NaOH was added in an amount such that the sum of the amount of NaOH and that previously added for pH adjustment was 75.67 g (1.892 mol). Thereafter, the reaction solution was stirred at 90° C. for 3 hours. During this period, nitrogen gas was blown into the reaction solution, thereby continuously eliminating generated ammonia gas from the system. Thereafter, the reaction solution was cooled to room temperature, and the pH thereof was adjusted to 1.0 with concentrated hydrochloric acid. A formed white precipitate was separated by filtration, washed with water and dried. Thus, 229.16 g (yield from glycine: 96.2%) of a white powder of N-carboxyethyl-N-tetradecanoylglycine represented by the following formula was obtained.

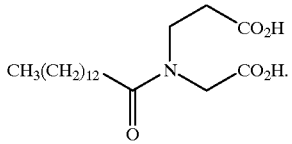

Infrared absorption spectrum (KBr)
3150 (b), 2924 (s), 2860 (s), 1724 (s), 1616 (s), 1478 (s), 1418 (m), 1258 (s), 1188 (s) cm$^{-1}$ $^1$H-NMR spectrum (200 MHz, $CDCl_3$) 10.4 (b,2 H), 4.19 (s,1 H), 4.17 (s,1 H), 3.67 (dd,2 H), 2.65 (t,2 H), 2.33 (t,1 H), 2.12 (t,1 H), 1.58 (m,2 H), 1.23 (b,16 H), 0.80 (t,3 H) ppm Elemental analysis ($C_{19}H_{35}NO_5$=357.49)
Calculated (%) C: 63.84, H: 9.87, N: 3.92, O: 22.38
Found (%) C: 63.71, H: 9.91, N: 3.90, O: 22.52

Test Example 1

The foaming power of each of the glycine derivatives according to the present invention and a comparative product was evaluated by the following method. The results are shown in Table 1.

Method of evaluating foaming power

A mixture (pH 7.0) of a surfactant (0.1% by weight), lanolin (0.3% by weight) and 4° DH hard water was foamed at 40° C. according to the Water Flash method. The volume of foam was measured 10 sec and 120 sec after the discontinuation of the foaming.

TABLE 1

| Surfactant | Volume of foam (ml) | |
| --- | --- | --- |
| | after 10 sec. | after 120 sec. |
| sodium N-cyanoethyl-N-dodecanoylglycinate obtained in Ex. 3 | 190 | 180 |
| potassium N-cyanoethyl-N-dodecanoylglycinate obtained in Ex. 4 | 180 | 165 |
| ammonium N-cyanoethyl-N-dodecanoylglycinate obtained in Ex. 5 | 180 | 150 |
| sodium N-carboxyethyl-N-dodecanoylglycinate obtained in Ex. 9 | 190 | 180 |
| potassium N-carboxyethyl-N-dodecanoylglycinate obtained in Ex. 10 | 180 | 165 |
| magnesium N-carboxyethyl-N-dedecanoylglycinate obtained in Ex. 11 | 175 | 155 |
| ammonium N-carboxyethyl-N-dodecanoylglycinate obtained in Ex. 12 | 190 | 150 |
| $C_{12}H_{25}(OCH_2CH_2)_{4.0}$—$OSO_3Na$ (comparative product 1) | 170 | 90 |

Test Example 2

With respect to each of the glycine derivative of the present invention and comparative products, the irritation to the skin was evaluated by the following method. The results are shown in Table 2.

Method of evaluating skin irritation

An aqueous surfactant solution (pH 7.0) having a concentration of 10% by weight was applied to the flank, whose hair had been cropped and shaved, of a white Hartley guinea pig (6 weeks old, female) once a day for four consecutive days, and the skin irritation was judged. For the judgment, the part where the solution was applied was observed 24 hours after the fourth application and the result of the observation was scored according to the following criteria. Table 2 shows the average of the scored evaluations (N=5).

Criteria:

0: no reaction observed;

1: slight erythema observed;

2: clear erythema observed;

3: clear erythema accompanied by edema; and

4: clear erythema accompanied by edema, crust and necrosis.

TABLE 2

| Surfactant | Average of scored evaluations |
| --- | --- |
| sodium N-carboxyethyl-N-dodecanoylglycinate obtained in Ex. 9 | 0.2 |
| $C_{12}H_{25}(OCH_2CH_2)_{4.0}$—$OSO_3Na$ (comparative product 1) | 2.2 |
| $C_{12}H_{25}$—$OSO_3Na$ (comparative product 2) | 2.6 |

Formulation examples of the cleanser compositions of the present invention will be described below.

Formulation Example 1

A shampoo (pH 5.0) having the following composition was prepared. The obtained shampoo not only was excellent in foaming power and detergency, but also ensured a good feeling in the washing and rinsing of the hair.

| | |
| --- | --- |
| sodium N-carboxyethyl-N-dodecanoyl-glycinate obtained in Example 9 | 15.0% by weight |
| lauroyldiethanolamide | 3.0 |
| lauryldimethylamine oxide | 0.5 |
| hydroxyethylcellulose (SE-850K produced by Daicel Chemical Industries, Ltd.) | 0.1 |
| sodium benzoate | appropriate amount |
| citric acid | appropriate amount |
| coloring matter | appropriate amount |
| fragrance | appropriate amount |
| water | balance |
| | 100% by weight in total |

Formulation Example 2

A shampoo (pH 4.5) having the following composition was prepared. The obtained shampoo not only was excellent in foaming power and detergency, but also ensured a good feeling in the washing and rinsing of the hair.

| | |
| --- | --- |
| sodium N-carboxyethyl-N-dodecanoyl-glycinate obtained in Example 9 | 10.0% by weight |
| sodium N-cyanoethyl-N-dodecanoyl-glycinate obtained in Example 3 | 5.0 |
| lauroyldiethanolamide | 3.0 |
| lauryldimethylamine oxide | 0.5 |
| hydroxyethylcellulose (SE-850K produced by Daicel Chemical Industries, Ltd.) | 0.1 |
| sodium benzoate | appropriate amount |
| phosphoric acid | appropriate amount |
| coloring matter | appropriate amount |
| fragrance | appropriate amount |
| water | balance |
| | 100% by weight in total |

Formulation Example 3

A body shampoo (pH 6.0) having the following composition was prepared. The obtained body shampoo was excellent in foaming power and detergency, and ensured a refreshed and good feeling during washing and rinsing and after washing.

| | |
| --- | --- |
| ammonium N-carboxyethyl-N-dodecanoyl-glycinate obtained in Example 12 | 15.0% by weight |
| lauryldimethylacetic acid betaine | 3.0 |
| lauric acid | 0.5 |
| sucrose fatty acid ester | 0.1 |
| sodium benzoate | appropriate amount |
| citric acid | appropriate amount |
| methylparaben | appropriate amount |
| coloring matter | appropriate amount |
| fragrance | appropriate amount |
| water | balance |
| | 100% by weight in total |

Formulation Example 4

A body shampoo (pH 5.0) having the following composition was prepared. The obtained body shampoo was excellent in foaming power and detergency, and ensured a refreshed and good feeling during washing and rinsing and after washing.

| | |
| --- | --- |
| sodium N-carboxyethyl-N-dodecanoyl-glycinate obtained in Example 9 | 10.0% by weight |
| sodium N-cyanoethyl-N-dodecanoyl-glycinate obtained in Example 3 | 5.0 |
| lauryldimethylamine oxide | 3.0 |
| lauric acid | 0.5 |
| sucrose fatty acid ester | 0.1 |
| sodium benzoate | appropriate amount |
| citric acid | appropriate amount |
| methylparaben | appropriate amount |
| coloring matter | appropriate amount |
| fragrance | appropriate amount |
| water | balance |
| | 100% by weight in total |

Test Example 3

The components of each of the cleanser compositions specified in Tables 3 and 4 were homogeneously mixed in the proportions specified therein, and the pH values of the resultant mixtures were adjusted with hydrochloric acid, thereby producing the cleanser compositions. The pH value of each of the cleanser compositions was determined by diluting the composition 10-fold by weight with water to thereby prepare an aqueous solution, taking 50 ml therefrom and measuring the pH thereof at 25° C. with the use of pH meter F-14 manufactured by Horiba.

The storage stability, foaming and comfort in use of each of the obtained cleanser compositions were evaluated according to the following criteria. The results are shown in Tables 3 and 4.

Evaluation methods (i) Storage stability 50 ml of each of the cleanser compositions was charged into a screwed glass tube, sealed and stored in a 5° C. thermostatic chamber for one month. Upon the lapse of this period, the liquid condition of the contents was visually observed and evaluated according to the following criterion:

○: the liquid was homogeneous and transparent, and x: crystals were formed, or the liquid was clouded.

(ii) Foaming

Each of the cleanser compositions was diluted 10-fold with water to thereby obtain an aqueous solution, and 100 ml (temperature of the solution: 40° C.) of the aqueous solution was poured into a graduated cylinder. Then, an agitation blade was set in the aqueous solution and revolved. The agitation blade was revolved at 1000 rpm, and its revolution was reversed every 5 seconds. The volume (ml) of foam formed 30 sec after the start of the agitation was measured and defined as the foaming volume, which was evaluated by the following criterion:

◎: foaming volume of 200 ml or more,
○: foaming volume of not less than 160 ml but less than 200 ml,
Δ: foaming volume of not less than 120 ml but less than 160 ml, and
x: less than 120 ml.

(iii) Comfort in use

Organoleptic evaluations with respect to the following items were carried out by having 10 panelists (men and women) conduct body cleansing for one week with the use of each of the cleanser compositions. The evaluations were made according to the following criteria and the average values thereof were calculated. When the average value was 4.5 or above, 3.5 to 4.4, 2.5 to 3.4 and 2.4 or below, the cleanser composition was judged, with respect to comfort in use, as being very excellent (◎), good (○), ordinary (Δ) and inferior (x), respectively.

(1) Foaming
5: good in foaming,
4: relatively good in foaming,
3: ordinary,
2: relatively poor in foaming, and
1: poor in foaming.

(2) Foam stability
5: good in foam stability,
4: relatively good in foam stability,
3: ordinary,
2: relatively poor in foam stability, and
1: poor in foam stability.

(3) Foam breaking during rinsing
5: good in foam breaking,
4: relatively good in foam breaking,
3: ordinary,
2: relatively poor in foam breaking, and
1: poor in foam breaking.

(4) Clean feeling at the time of towel drying
5: clean,
4: relatively clean,
3: ordinary,
2: relatively slimy and sticky, and
1: slimy and sticky.

TABLE 3

| Components (%) | Invention product | | | | | | |
|---|---|---|---|---|---|---|---|
| | 1 | 2 | 3 | 4 | 5 | 6 | 7 |
| sodium N-carboxyethyl-N-dodecanoylglycinate* | 20 | 15 | 10 | — | — | — | — |
| potassium N-carboxyethyl-N-dodecanoylglycinate* | — | — | — | 20 | — | — | — |
| triethanolamine salt of N-carboxyethyl-N-dodecanoylglycine* | — | — | — | — | 20 | — | — |
| arginine salt of N-carboxyethyl-N-dodecanoylglycine* | — | — | — | — | — | 20 | — |
| sodium N-carboxyethyl-N-tetradecanoylglycinate* | — | — | — | — | — | — | 20 |
| sodium N-lauroyl-N-iminodiacetate* | — | — | — | — | — | — | — |
| sodium N-lauroyl-N-iminodipropionate* | — | — | — | — | — | — | — |
| alkylsaccharide ($R^1 = C_{12}H_{25}$, m = 0, G = glucose and n = 1.3 in formula (7)) | 10 | 15 | 20 | 10 | 10 | 10 | 10 |
| purified water | balance | balance | balance | balance | balance | balance | balance |
| pH | 6.0 | 6.2 | 6.0 | 6.1 | 6.0 | 6.0 | 6.0 |
| storage stability (5° C.) | ○ | ○ | ○ | ○ | ○ | ○ | ○ |
| foaming (40° C.) | ◎ | ◎ | ◎ | ◎ | ○ | ◎ | ◎ |
| comfort in use (1) foaming | ◎ | ◎ | ◎ | ◎ | ○ | ◎ | ○ |
| (2) foam stability | ◎ | ◎ | ○ | ◎ | ○ | ◎ | ◎ |
| (3) foam breaking during rinsing | ◎ | ◎ | ○ | ◎ | ○ | ◎ | ◎ |
| (4) clean feeling at towel drying | ◎ | ◎ | ○ | ◎ | ○ | ◎ | ◎ | note)
*: it can be present in the form of mono salt, di salt, or a mixture of mono salt and di salt.

TABLE 4

| Component (%) | Comparative product | | |
|---|---|---|---|
| | 1 | 2 | 3 |
| sodium N-carboxyethyl-N-dodecanoylglycinate* | — | — | — |
| potassium N-carboxyethyl-N-dodecanoylglycinate* | — | — | — |
| triethanolamine salt of N-carboxyethyl-N-dodecanoylglycine* | — | — | — |
| arginine salt of N-carboxyethyl-N-dodecanoylglycine* | — | — | — |
| sodium N-carboxyethyl-N-tetradecanoylglycinate* | — | — | — |
| sodium N-lauroyl-N-iminodiacetate* | 20 | — | — |
| sodium N-lauroyl-N-iminodipropionate* | — | 20 | — |
| alkylsaccharide ($R^1 = C_{12}H_{25}$, m = 0, G = glucose and n = 1.3 in the formula (7)) | 10 | 10 | 30 |
| purified water | balance | balance | balance |
| pH | 6.0 | 6.1 | 6.1 |
| storage stability (5° C.) | X | X | ○ |
| foaming (40° C.) | X | Δ | Δ |
| comfort in use (1) foaming | X | Δ | Δ |
| (2) foam stability | X | Δ | X |
| (3) foam breaking during rinsing | Δ | Δ | Δ |
| (4) clean feeling at towel drying | Δ | Δ | Δ | note)
*: it can be present in the form of mono salt, di salt, or a mixture of mono salt and di salt.

The cleanser compositions of the present invention were excellent in storage stability, foaming, and comfort in use thereof, as apparent from the results shown in Tables 3 and 4. Further, they were also excellent in detergency, and their irritancy to the skin was extremely low.

Formulation examples of the cleanser compositions of the present invention will be described below.

Formulation Example 5 (whole-body cleanser)

| Components | |
|---|---|
| (1) sodium N-carboxyethyl-N-dodecanoylglycinate* | 20% by weight |
| (2) alkylsaccharide ($R^1 = C_{10}H_{21}$, m = 0, G = glucose and n = 11 in formula (7)) | 5 |
| (3) methylcellulose | 0.1 |
| (4) fragrance | 0.5 |
| (5) ethanol | 3 |
| (6) sodium hydroxide | 2 |
| (7) purified water | balance |
| | 100% by weight in total |

*: it can be present in the form of mono salt, di salt, or a mixture of mono salt and di salt.

Process for production

Components (1) and (6) were added to hot purified water (7) and dissolved therein. After the resultant aqueous solution was cooled, components (2) to (5) were added thereto, thereby obtaining a transparent liquid cleanser composition. The pH of an aqueous solution obtained by diluting the resultant cleanser composition 10-fold by weight with water was 6.0.

When the obtained liquid cleanser composition was used in cleansing the skin and hair, the cleanser composition was excellent in the foaming and rinsability, gave a clean feeling and was excellent in comfort in use thereof. Also, its irritation to the skin was low, and the storage stability thereof was excellent.

Formulation Example 6 (face cleanser)

| Components | |
|---|---|
| (1) N-carboxyethyl-N-dodecanolyglycine | 20% by weight |
| (2) arginine | 12 |
| (3) alkylsaccharide ($R^1 = C_{10}H_{21}$, m = 0, G = glucose and n = 11 in formula (7)) | 10 |
| (4) lauryldimethylamine oxide | 3 |
| (5) fragrance | 0.5 |
| (6) sodium hydroxide | appropriate amt. |
| (7) purified water | balance |
| | 100% by weight in total |

Process for production

Component (2) and subsequently component (1) were added to hot purified water (7) to thereby neutralize and dissolve. After the resultant aqueous solution was cooled, components (3) to (5) were added thereto, thereby obtaining a transparent liquid cleanser composition. The pH of an aqueous solution obtained by diluting the resultant cleanser composition 10-fold by weight with water was 6.5.

The use of the obtained liquid cleanser composition in cleansing the face demonstrated that the cleanser composition was excellent in foaming and rinsability, gave a clean feeling, did not give a feeling of stiffness after drying, and was also excellent in the comfort in use thereof. Further, its irritation to the skin was low, and the storage stability thereof was excellent.

Test Example 4

The components of each of the cleanser compositions specified in Tables 5 and 6 were homogeneously mixed in the proportions specified therein, and the pH values of the resultant mixtures were adjusted with hydrochloric acid, thereby producing the cleanser compositions. The pH value of each of the cleanser compositions was determined by diluting the composition 10-fold by weight with water to thereby prepare an aqueous solution, taking 50 ml therefrom and measuring the pH thereof at 25° C. with the use of pH meter F-14 manufactured by Horiba.

The storage stability, foaming, and comfort in use of each of the obtained cleanser compositions were evaluated. The evaluation methods were the same as those in Test Example 3. The results are shown in Tables 5 and 6.

TABLE 5

| | Invention product | | | | | | |
|---|---|---|---|---|---|---|---|
| Components (%) | 8 | 9 | 10 | 11 | 12 | 13 | 14 |
| sodium N-carboxyethyl-N-dodecanoylglycinate* | 22 | 20 | 15 | 20 | — | — | — |
| potassium N-carboxyethyl-N-dodecanoylglycinate* | — | — | — | — | 20 | — | — |
| triethanolamine salt of N-carboxyethyl-N-dodecanoylglycine* | — | — | — | — | — | 20 | — |
| arginine salt of N-carboxyethyl-N-dodecanoylglycine* | — | — | — | — | — | — | 20 |
| sodium N-carboxyethyl-N-tetradecanoylglycinate* | — | — | — | — | — | — | — |
| sodium N-lauroyl-N-iminodiacetate* | — | — | — | — | — | — | — |
| sodium N-lauroyl-N-iminodipropionate* | — | — | — | — | — | — | — |
| mono(polyoxyethylene (3) lauramide ether)methane carboxylic acid | 3 | 5 | 10 | — | 5 | 5 | 5 |
| mono(polyoxyethylene (6) fatty amide ether)methanecarboxylic acid (acyl group: $C_{12}/C_{14} = 75/25$) | — | — | — | 5 | — | — | — |
| purified water | balance | balance | balance | balance | balance | balance | balance |
| pH | 6.1 | 6.0 | 6.0 | 6.1 | 6.0 | 6.0 | 6.0 |
| storage stability (5° C.) | ○ | ○ | ○ | ○ | ○ | ○ | ○ |
| foaming (40° C.) | ⊚ | ⊚ | ⊚ | ⊚ | ⊚ | ○ | ⊚ |
| comfort (1) foaming | ⊚ | ⊚ | ⊚ | ⊚ | ⊚ | ○ | ⊚ |

TABLE 5-continued

|  |  | Invention product | | | | | | |
|---|---|---|---|---|---|---|---|---|
| Components (%) | | 8 | 9 | 10 | 11 | 12 | 13 | 14 |
| in use | (2) foam stability | ⊚ | ⊚ | ⊚ | ○ | ⊚ | ○ | ⊚ |
|  | (3) foam breaking during rinsing | ⊚ | ⊚ | ⊚ | ○ | ⊚ | ○ | ⊚ |
|  | (4) clean feeling at towel drying | ⊚ | ⊚ | ⊚ | ○ | ⊚ | ○ | ⊚ | note)
*: it can be present in the form of mono salt, di salt, or a mixture of mono salt and di salt.

TABLE 6

|  | Invention product | | Comparative product | | | | |
|---|---|---|---|---|---|---|---|
| Components (%) | 15 | 16 | 4 | 5 | 6 | 7 | 8 |
| sodium N-carboxyethyl-N-dodecanoylglycinate* | — | — | — | — | — | — | — |
| potassium N-carboxyethyl-N-dodecanoylglycinate* | — | — | — | — | — | — | — |
| triethanolamine salt of N-carboxyethyl-N-dodecanoylglycine* | — | — | — | — | — | — | — |
| arginine salt of N-carboxyethyl-N-dodecanoylglycine* | — | — | — | — | — | — | — |
| sodium N-carboxyethyl-N-tetradecanoylglycinate* | 20 | 20 | — | — | — | — | — |
| sodium N-lauroyl-N-iminodiacetate* | — | — | 20 | 15 | 20 | — | — |
| sodium N-lauroyl-N-iminodipropionate* | — | — | — | — | — | 20 | — |
| mono(polyoxyethylene (3) lauramide ether)methane carboxylic acid | 5 | — | 5 | 10 | — | 5 | 25 |
| mono(polyoxyethylene (6) fatty amide ether)methane carboxylic acid (acyl group: $C_{12}/C_{14}$ = 75/25) | — | 5 | — | — | 5 | — | — |
| purified water | balance | balance | balance | balance | balance | balance | balance |
| pH | 5.9 | 6.0 | 6.0 | 5.9 | 6.0 | 6.0 | 6.1 |
| storage stability (5° C.) | ○ | ○ | X | X | X | X | ○ |
| foaming (40° C.) | ⊚ | ⊚ | X | X | X | X | Δ |
| comfort (1) foaming | ⊚ | ⊚ | X | X | X | X | Δ |
| in use (2) foam stability | ⊚ | ⊚ | X | X | X | Δ | X |
| (3) foam breaking during rinsing | ⊚ | ⊚ | X | X | Δ | X | X |
| (4) clean feeling at towel drying | ⊚ | ⊚ | X | X | Δ | X | X | note)
*: it can be present in the form of mono salt, di salt, or a mixture of mono salt and di salt.

The cleanser compositions of the present invention were excellent in storage stability, foaming, and comfort in use thereof, as apparent from the results shown in Tables 5 and 6. Further, they were also excellent in detergency, and their irritation to the skin was extremely low.

Formulation examples of the cleanser compositions of the present invention will be described below.

Formulation Example 7 (whole-body cleanser)

| Components | |
|---|---|
| (1) sodium N-carboxyethyl-N-dodecanoylglycinate* | 20% by weight |
| (2) sodium salt of mono(polyoxyethylene (2) fatty amide ether)methane carboxylic acid (acyl group: $C_{12}/C_{14}$ = 75/25) | 5 |
| (3) methylcellulose | 0.1 |
| (4) fragrance | 0.5 |
| (5) ethanol | 3 |
| (6) purified water | balance |
| | 100% by weight in total |

*: it can be present in the form of mono salt, di salt, or a mixture of mono salt and di salt.

Process for production

Components (1) and (2) were added to hot purified water (6) and dissolved therein. After the resultant aqueous solution was cooled, components (3) to (5) were added thereto, thereby obtaining a transparent liquid cleanser composition. The pH of an aqueous solution obtained by diluting the resultant cleanser composition 10-fold by weight with water was 6.0.

When the obtained liquid cleanser composition was used in cleansing the skin and hair, the cleanser composition was excellent in foaming and rinsability, gave a clean feeling and was excellent in comfort in use thereof. Also, its irritation to the skin was low, and the storage stability thereof was excellent.

Formulation Example 8 (face cleanser)

| Components | |
|---|---|
| (1) N-carboxyethyl-N-dodecanolyglycine | 15% by weight |
| (2) N-carboxyethyl-N-tetradecanolyglycine | 5 |
| (3) arginine | 8 |
| (4) sodium salt of mono(polyoxyethylene (4) lauramide ether)methane carboxylic acid | 5 |

-continued

| Components | |
|---|---|
| (5) lauryldimethylamine oxide | 3 |
| (6) fragrance | 0.5 |
| (7) purified water | balance |
| | 100% by weight in total |

Process for production

Component (3) and subsequently components (1) and (2) were added to hot purified water (7) to thereby neutralize and dissolve. After the resultant aqueous solution was cooled, components (4) to (6) were added thereto, thereby obtaining a transparent liquid cleanser composition.

The use of the obtained liquid cleanser composition in cleansing the face demonstrated that the cleanser composition was excellent in foaming and rinsability, gave a clean feeling, did not give a feeling of stiffness after drying, and was also excellent in the comfort in use thereof.

Test Example 5

The components of each of the cleanser compositions specified in Tables 7 and 8 were homogeneously mixed in the proportions specified therein, and the pH values of the resultant mixtures were adjusted with hydrochloric acid, thereby producing the cleanser compositions. The pH value of each of the cleanser compositions was determined by diluting the composition 10-fold by weight with water to thereby prepare an aqueous solution, taking 50 ml therefrom and measuring the pH thereof at 25° C. with the use of pH meter F-14 manufactured by Horiba.

The storage stability, foaming, and comfort in use of each of the obtained cleanser compositions were evaluated. The evaluation methods were the same as those in Test Example 3. The results are shown in Tables 7 and 8.

TABLE 7

| | Invention product | | | | | | |
|---|---|---|---|---|---|---|---|
| Components (%) | 17 | 18 | 19 | 20 | 21 | 22 | 23 |
| sodium N-carboxyethyl-N-dodecanoylglycinate* | 22 | 20 | 20 | 20 | — | — | — |
| potassium N-carboxyethyl-N-dodecanoylglycinate* | — | — | — | — | 20 | — | — |
| triethanolamine salt of N-carboxyethyl-N-dodecanoylglycine* | — | — | — | — | — | 20 | — |
| arginine salt of N-carboxyethyl-N-dodecanoylglycine* | — | — | — | — | — | — | 20 |
| sodium N-carboxyethyl-N-tetradecanoylglycinate* | — | — | — | — | — | — | — |
| sodium N-lauroyl-N-iminodiacetate* | — | — | — | — | — | — | — |
| sodium N-lauroyl-N-iminodipropionate* | — | — | — | — | — | — | — |
| lauroyl monoethanolamide | 3 | 5 | — | — | — | 5 | 5 |
| lauroyl diethanolamide | — | — | 5 | — | 5 | — | — |
| coconut fatty acid diethanolamide | — | — | — | 5 | — | — | — |
| purified water | balance | balance | balance | balance | balance | balance | balance |
| pH | 6.0 | 6.0 | 6.0 | 6.0 | 6.0 | 6.0 | 6.0 |
| storage stability (5° C.) | ○ | ○ | ○ | ○ | ○ | ○ | ○ |
| foaming (40° C.) | ⊙ | ⊙ | ⊙ | ⊙ | ⊙ | ○ | ⊙ |
| comfort (1) foaming | ⊙ | ⊙ | ⊙ | ⊙ | ⊙ | ○ | ⊙ |
| in use (2) foam stability | ○ | ⊙ | ⊙ | ⊙ | ⊙ | ○ | ⊙ |
| (3) foam breaking during rinsing | ⊙ | ⊙ | ⊙ | ⊙ | ⊙ | ○ | ⊙ |
| (4) clean feeling at towel drying | ⊙ | ⊙ | ○ | ⊙ | ⊙ | ○ | ⊙ | note)
*: it can be present in the form of mono salt, di salt, or a mixture of mono salt and di salt.

TABLE 8

| | Invention product | | Comparative product | | | |
|---|---|---|---|---|---|---|
| Components (%) | 24 | 25 | 9 | 10 | 11 | 12 |
| sodium N-carboxyethyl-N-dodecanoylglycinate* | — | — | — | — | — | — |
| potassium N-carboxyethyl-N-dodecanoylglycinate* | — | — | — | — | — | — |
| triethanolamine salt of N-carboxyethyl-N-dodecanoylglycine* | — | — | — | — | — | — |
| arginine salt of N-carboxyethyl-N-dodecanoylglycine* | — | — | — | — | — | — |
| sodium N-carboxyethyl-N-tetradecanoylglycinate* | 20 | 20 | — | — | — | — |
| sodium N-lauroyl-N-iminodiacetate* | — | — | 20 | 20 | 20 | — |
| sodium N-lauroyl-N-iminodipropionate* | — | — | — | — | — | 20 |
| lauroyl monoethanolamide | — | — | 5 | — | — | 5 |
| lauroyl diethanolamide | 5 | — | — | 5 | — | — |
| coconut fatty acid diethanolamide | — | 5 | — | — | 5 | — |
| purified water | balance | balance | balance | balance | balance | balance |
| pH | 6.0 | 6.0 | 6.0 | 6.0 | 6.0 | 6.0 |
| storage stability (5° C.) | ○ | ○ | X | X | X | X |
| foaming (40° C.) | ⊙ | ⊙ | X | X | X | Δ |

TABLE 8-continued

| | | Invention product | | Comparative product | | | |
|---|---|---|---|---|---|---|---|
| Components (%) | | 24 | 25 | 9 | 10 | 11 | 12 |
| comfort in use | (1) foaming | ◯ | ◯ | X | X | X | Δ |
| | (2) foam stability | ⊚ | ⊚ | X | X | X | Δ |
| | (3) foam breaking during rinsing | ⊚ | ⊚ | Δ | Δ | Δ | Δ |
| | (4) clean feeling at towel drying | ⊚ | ⊚ | Δ | X | X | Δ | note)
*: it can be present in the form of mono salt, di salt, or a mixture of mono salt and di salt.

The cleanser compositions of the present invention were excellent in storage stability, foaming, and comfort in use thereof, as apparent from the results shown in Tables 7 and 8. Further, they were also excellent in detergency, and their irritation to the skin was extremely low.

Formulation examples of the cleanser compositions of the present invention will be described below.

Formulation Example 9 (whole-body cleanser)

| Components | |
|---|---|
| (1) sodium N-carboxyethyl-N-dodecanoylglycinate* | 15% by weight |
| (2) sodium N-carboxyethyl-N-tetradecanoylglycinate* | 5 |
| (3) lauroyl diethanolamide | 5 |
| (4) methylcellulose | 0.1 |
| (5) fragrance | 0.5 |
| (6) ethanol | 3 |
| (7) purified water | balance |
| | 100% by weight in total |

*: it can be present in the form of mono salt, di salt, or a mixture of mono salt and di salt.

Process for production

Components (1) and (2) were added to hot purified water (7) and dissolved therein. Then, components (3) to (6) were added thereto and mixed therewith. The resultant aqueous solution was cooled, and thus a transparent liquid cleanser composition (whole-body cleanser) was obtained. The pH of an aqueous solution obtained by diluting the resultant cleanser 10-fold by weight with water was 6.0.

When the obtained liquid cleanser was used for cleansing the skin and hair, the cleanser was excellent in foaming and rinsability, gave a clean feeling and was excellent comfort in use thereof. Also, its irritation to the skin was low, and the storage stability thereof was excellent.

Formulation Example 10 (face cleanser)

| Components | |
|---|---|
| (1) N-carboxyethyl-N-dodecanoyl-glycine | 12% by weight |
| (2) N-carboxyethyl-N-tetradecanoly-glycine | 8 |
| (3) arginine | 8 |
| (4) coconut fatty acid monoethanolamide | 5 |

-continued

| Components | |
|---|---|
| (5) glycerol | 10 |
| (6) fragrance | 0.5 |
| (7) purified water | balance |
| | 100% by weight in total |

Process for production

Component (3) and subsequently components (1) and (2) were added to hot purified water (7) to thereby neutralize and dissolve. Then, components (4) and (5) were added thereto and mixed therewith. After the resultant aqueous solution was cooled, component (6) was added thereto, thereby obtaining a transparent liquid cleanser composition (face cleanser). The pH of an aqueous solution obtained by diluting the resultant face cleanser 10-fold by weight with water was 6.0.

The use of the obtained face cleanser for cleansing the face demonstrated that the face cleanser was excellent in foaming and rinsability, gave a clean feeling, did not give feeling of stiffness after drying, and was also excellent in the comfort in use thereof. Also, its irritation to the skin was low, and the storage stability thereof was excellent.

This application is based on Japanese Patent Application No. 6-58853, filed Mar. 29, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed is:

1. A glycine derivative represented by the following formula (1):

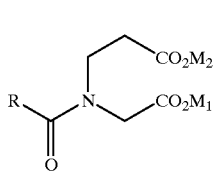

(1)

wherein R is a linear or branched alkyl group having 11 to 13 carbon atoms, a linear or branched alkenyl group having 11 to 13 carbon atoms, or a linear or branched hydroxyalkyl group having 11 to 13 carbon atoms, and $M_1$ and $M_2$ are the same or different from each other and each independently is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid.

2. The glycine derivative of claim 1, wherein R is a linear or branched alkyl group having 11 to 13 carbon atoms or a linear or branched alkenyl group having 11 to 13 carbon atoms, and $M_1$ and $M_2$ are the same or different from each other and each independently is a hydrogen atom, a sodium atom, a potassium atom, ½ (a magnesium atom), an ammonium group, a monoethanolammonium group, a diethanolammonium group or a triethanolammonium group.

3. The glycine derivative of claim 1, wherein R is a linear alkyl group having 11 to 13 carbon atoms, and $M_1$ and $M_2$ are the same or different from each other and each independently is a hydrogen atom, a sodium atom, a potassium atom or an ammonium group.

4. A glycine derivative represented by the following formula (2):

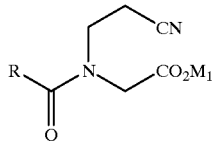

(2)

wherein R is a linear or branched alkyl group having 11 to 13 carbon atoms, a linear or branched alkenyl group having 11 to 13 carbon atoms, or a linear or branched hydroxyalkyl group having 11 to 13 carbon atoms, and $M_1$ is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid.

5. A glycine derivative represented by the following formula (3):

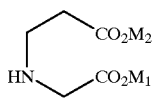

(3)

wherein $M_1$ and $M_2$ are the same or different from each other and each independently is, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid.

6. A glycine derivative represented by the following formula (4):

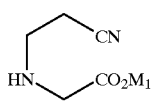

(4)

wherein $M_1$ is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid.

7. A process for producing a glycine derivative represented by the following formula (1):

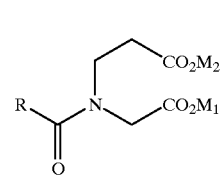

(1)

wherein R is a linear or branched alkyl group having 11 to 13 carbon atoms, a linear or branched alkenyl group having 11 to 13 carbon atoms, or a linear or branched hydroxyalkyl group having 11 to 13 carbon atoms, and $M_1$ and $M_2$ are the same or different from each other and each independently is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid, which comprises hydrolyzing the cyano group of a glycine derivative represented by the following formula (2), optionally followed by salt exchange:

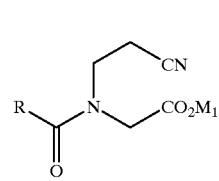

(2)

wherein R and $M_1$ are each as defined above.

8. A process for producing a glycine derivative represented by the following formula (1):

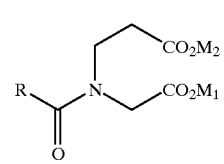

(1)

wherein R is a linear or branched alkyl group having 11 to 13 carbon atoms, a linear or branched alkenyl group having 11 to 13 carbon atoms, or a linear or branched hydroxyalkyl group having 11 to 13 carbon atoms, and $M_1$ and $M_2$ are the same or different from each other and each independently is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid, which comprises reacting a glycine derivative resented by the following formula (3):

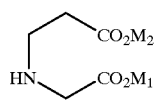

(3)

wherein $M_1$ and $M_2$ are each as defined above, with an acid chloride represented by the following formula (6), optionally followed by salt exchange:

RCOCl (6)

wherein R is as defined above.

9. A process for producing a glycine derivative represented by the following formula (2):

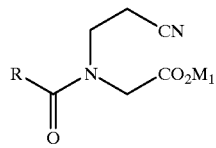

(2)

wherein R is a linear or branched alkyl group having 11 to 13 carbon atoms, a linear or branched alkenyl group having 11 to 13 carbon atoms, or a linear or branched hydroxyalkyl group having 11 to 13 carbon atoms, and $M_1$ is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid, which comprises reacting a glycine derivative represented by the following formula (4):

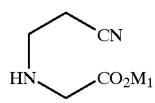

(4)

wherein $M_1$ is as defined above,
with an acid chloride represented by the following formula (6), optionally followed by salt exchange:

RCOCl (6)

wherein R is as defined above.

10. A process for producing a glycine derivative represented by the following formula (3):

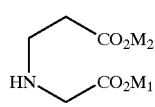

(3)

wherein $M_1$ and $M_2$ are the same or different from each other and each independently is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid, which comprises hydrolyzing the cyano group of a glycine derivative represented by the following formula (4), optionally followed by salt exchange:

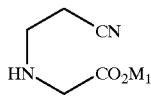

(4)

wherein $M_1$ is as defined above.

11. A process for producing a glycine derivative represented by the following formula (4):

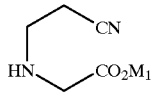

(4)

wherein $M_1$ is a hydrogen atom, an alkali metal atom, ½ (an alkaline earth metal atom), an ammonium group, a monoalkanolammonium group having 1 to 22 carbon atoms, dialkanolammonium group having 2 to 22 carbon atoms in total, a trialkanolammonium group having 3 to 22 carbon atoms in total, or a protonated basic amino acid, which comprises reacting glycine or a salt thereof represented by the following formula (5) with acrylonitrile:

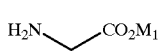

(5)

wherein $M_1$ is as defined above.

12. A process for producing a glycine derivative represented by the following formula (2):

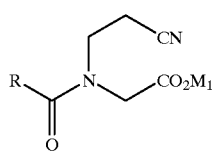

(2)

wherein R is a linear or branched alkyl group having 11 to 13 carbon atoms, a linear or branched alkenyl group having 11 to 13 carbon atoms, or a linear or branched hydroxyalkyl group having 11 to 13 carbon atoms, and $M_1$ is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid, which comprises a step of reacting glycine or a salt thereof represented by the following formula (5):

(5)

wherein $M_1$ is as defined above, with acrylonitrile to give a glycine derivative represented by the following formula (4):

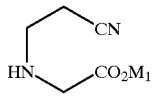

(4)

wherein $M_1$ is as defined above, and a step of reacting the glycine derivative represented by the above formula (4) with an acid chloride represented by the following formula (6), optionally followed by salt exchange:

RCOCl (6)

wherein R is as defined above.

13. A process for producing a glycine derivative represented by the following formula (1):

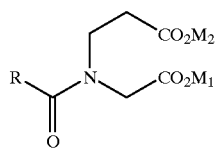

(1)

wherein R is a linear or branched alkyl group having 11 to 13 carbon atoms, a linear or branched alkenyl group having 11 to 13 carbon atoms, or a linear or branched hydroxyalkyl group having 11 to 13 carbon atoms, and $M_1$ and $M_2$ are the same or different from each other and each independently is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid, which comprises a step of reacting glycine or a salt thereof represented by the following formula (5):

(5)

wherein $M_1$ is as defined above, with acrylonitrile to give a glycine derivative represented by the following formula (4):

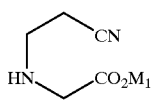

(4)

wherein $M_1$ is as defined above, and a step of hydrolyzing the cyano group of the glycine derivative represented by the above formula (4), optionally followed by salt exchange.

14. A process for producing a glycine derivative represented by the following formula (3):

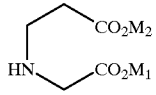

(3)

wherein $M_1$ and $M_2$ are the same or different from each other and each independently is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid, which comprises a step of reacting glycine or a salt thereof represented by the following formula (5):

(5)

wherein $M_1$ is as defined above, with acrylonitrile to give a glycine derivative represented by the following formula (4):

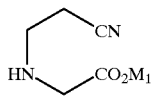

(4)

wherein $M_1$ is as defined above, and a step of hydrolyzing the cyano group of the glycine derivative represented by the above formula (4), optionally followed by salt exchange.

15. A process for producing a glycine derivative represented by the following formula (1):

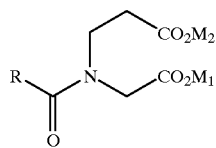

(1)

wherein R is a linear or branched alkyl group having 11 to 13 carbon atoms, a linear or branched alkenyl group having 11 to 13 carbon atoms, or a linear or branched hydroxyalkyl group having 11 to 13 carbon atoms, and $M_1$ and $M_2$ are the same or different from each other and each independently is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid, which comprises a step of reacting glycine or a salt thereof represented by the following formula (5):

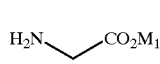

(5)

wherein $M_1$ is as defined above, with acrylonitrile to give a glycine derivative represented by the following formula (4):

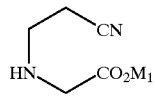

(4)

wherein $M_1$ is as defined above, a step of reacting the glycine derivative represented by the above formula (4) with an acid chloride represented by the following formula (6):

RCOCl (6)

wherein R is as defined above, optionally followed by salt exchange to give a glycine derivative represented by the following formula (2):

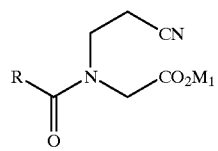

(2)

wherein R and $M_1$ are each as defined above, and a step of hydrolyzing the cyano group of the glycine derivative represented by the above formula (2), optionally followed by salt exchange.

16. A process for producing a glycine derivative represented by the following formula (1):

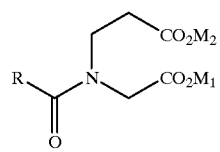

(1)

wherein R is a linear or branched alkyl group having 11 to 13 carbon atoms, a linear or branched alkenyl group having 11 to 13 carbon atoms, or a linear or branched hydroxyalkyl group having 11 to 13 carbon atoms, and $M_1$ and $M_2$ are the same or different from each other and each independently is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid, which comprises a step of reacting glycine or a salt thereof represented by the following formula (5):

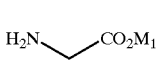

(5)

wherein $M_1$ is as defined above, with acrylonitrile to give a glycine derivative represented by the following formula (4):

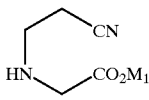

(4)

wherein $M_1$ is as defined above, a step of hydrolyzing the cyano group of the glycine derivative represented by the above formula (4), optionally followed by salt exchange to give a glycine derivative represented by the following formula (3):

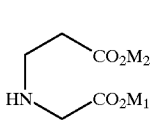

(3)

wherein $M_1$ and $M_2$ are each as defined above, and a step of reacting the glycine derivative represented by the above formula (3) with an acid chloride represented by the following formula (6), optionally followed by salt exchange:

RCOCl (6)

wherein R is as defined above.

17. A cleanser composition comprising a glycine derivative represented by the following formula (1):

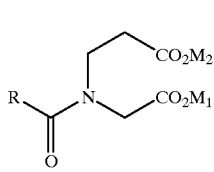

(1)

wherein R is a linear or branched alkyl group having 11 to 13 carbon atoms, a linear or branched alkenyl group having 11 to 13 carbon atoms, or a linear or branched hydroxyalkyl group having 11 to 13 carbon atoms, and $M_1$ and $M_2$ are the same or different from each other and each independently is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid.

18. The cleanser composition of claim 17, which further comprises a sugar surfactant represented by the following formula (7):

(7)

wherein $R^1$ is a linear or branched alkyl group having 8 to 18 carbon atoms, a linear or branched alkenyl group having 8 to 18 carbon atoms, or a substituted phenyl group having a linear or branched alkyl group of 8 to 18 carbon atoms, $R^2$ is an alkylene group having 2 to 4 carbon atoms, G is a residue derived from a reducing sugar having 5 to 6 carbon atoms, m is a number of 0 to 10 and n is a number of 1 to 10.

19. The cleanser composition of claim 17, which further comprises an ether-type acetic acid surfactant represented by the following formula (8):

$$R^3-Z-(CH_2CH_2O)_l-CH_2CO_2X \tag{8}$$

wherein $R^3$ is a linear or branched alkyl group having 5 to 21 carbon atoms, or a linear or branched alkenyl group having 5 to 21 carbon atoms, Z is a group represented by the formula: —O— or a group represented by the formula: —CONH—, X is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total or a protonated basic amino acid, and l is a number of 2 to 15.

20. The cleanser composition of claim 17, which further comprises a fatty acid amide derivative represented by the following formula (9):

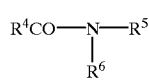

wherein $R^4$ is a linear or branched alkyl group having 7 to 21 carbon atoms, and $R^5$ and $R^6$ are the same or different from each other and each independently is a hydrogen atom, an alkyl group having 1 to 3 carbon atoms, a hydroxyalkyl group having 1 to 3 carbon atoms or a group represented by the formula: —$(C_2H_4O)_kH$ (wherein k is a number of 2 to 4).

21. A cleanser composition comprising a glycine derivative represented by the following formula (2):

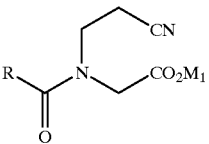

wherein R is a linear or branched alkyl group having 11 to 13 carbon atoms, a linear or branched alkenyl group having 11 to 13 carbon atoms, or a linear or branched hydroxyalkyl group having 11 to 13 carbon atoms, and $M_1$ is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid.

22. A method of washing skin or hair which comprises contacting said skin or hair with a composition comprising a glycine derivative represented by the following formula (1):

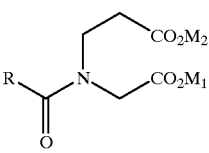

wherein R is a linear or branched alkyl group having 11 to 13 carbon atoms, a linear or branched alkenyl group having 11 to 13 carbon atoms, or a linear or branched hydroxyalkyl group having 11 to 13 carbon atoms, and $M_1$ and $M_2$ are the same or different from each other and each independently is a hydrogen atom, an alkali metal atom, ½ (an alkaline earth metal atom), an ammonium group, a monoalkanolammonium group having 1 to 22 carbon atoms, a dialkanolammonium group having 2 to 22 carbon atoms in total, a trialkanolammonium group having 3 to 22 carbon atoms in total, or a protonated basic amino acid.

* * * * *